United States Patent
Monteil et al.

(10) Patent No.: US 9,828,470 B2
(45) Date of Patent: Nov. 28, 2017

(54) SILICONE COMPOSITION THAT CAN BE CURED IN THE PRESENCE OF WATER OR ATMOSPHERIC MOISTURE

(71) Applicants: Bluestar Silicones France SAS, Lyons (FR); Universite Claude Bernard Lyon 1, Villeurbanne (FR); Centre National De La Recherche Scientifique, Paris (FR)

(72) Inventors: Vincent Monteil, Lyons (FR); Roger Spitz, Lyons (FR); Aurelie Mondiere, Lyons (FR); Tania Ireland, Cessieu (FR); Anne Seggio, Lyons (FR)

(73) Assignees: BLUESTAR SILICONES FRANCE SAS, Lyons (FR); UNIVERSITE CLAUDE BERNARD LYON 1, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/039,646

(22) PCT Filed: Dec. 3, 2014

(86) PCT No.: PCT/FR2014/053141
§ 371 (c)(1),
(2) Date: May 26, 2016

(87) PCT Pub. No.: WO2015/082837
PCT Pub. Date: Jun. 11, 2015

(65) Prior Publication Data
US 2017/0022325 A1    Jan. 26, 2017

(30) Foreign Application Priority Data
Dec. 3, 2013   (FR) ..................... 13 62008

(51) Int. Cl.
| | |
|---|---|
| C08G 77/08 | (2006.01) |
| C07F 7/00 | (2006.01) |
| C09D 183/04 | (2006.01) |
| C08K 5/56 | (2006.01) |
| B05D 3/00 | (2006.01) |
| C08K 5/544 | (2006.01) |
| B01J 31/22 | (2006.01) |
| C08G 77/16 | (2006.01) |

(52) U.S. Cl.
CPC ............. *C08G 77/08* (2013.01); *B05D 3/007* (2013.01); *C07F 7/006* (2013.01); *C08K 5/544* (2013.01); *C08K 5/56* (2013.01); *C09D 183/04* (2013.01); *B01J 31/2226* (2013.01); *B01J 2531/22* (2013.01); *B01J 2531/31* (2013.01); *B01J 2531/46* (2013.01); *B01J 2531/48* (2013.01); *C08G 77/16* (2013.01)

(58) Field of Classification Search
None
See application file for complete search history.

(56) References Cited

U.S. PATENT DOCUMENTS 5,502,144 A * 3/1996 Kuo ................. C08L 83/04
528/18
2013/0295298 A1   11/2013 Gatineau et al.

FOREIGN PATENT DOCUMENTS

FR        2856694 A1    6/2003

OTHER PUBLICATIONS

Singh et al. "Novel heterometallic alkoxide coordination systems of polyols (glycols, di- and tri-ethanolamines) derived from the corrsponding homometallic moieites" Coordination Chemistry Reviews, 248, 2004, 101-118.*
International Search Report dated Mar. 19, 2015 in counterpart French Application No. PCT/FR2014/053141.

* cited by examiner

*Primary Examiner* — Robert S Loewe
(74) *Attorney, Agent, or Firm* — McBee Moore Woodward & Vanik IP, LLC

(57) ABSTRACT

The invention concerns compositions that can be cured in the presence of water or atmospheric moisture comprising at least one polyorganosiloxane having one or a plurality of condensable group(s) or hydrolysable and condensable group(s) and at least one compound capable of catalyzing the condensation reaction of the condensable or hydrolysable and condensable groups of the polyorganosiloxane. This compound is a heterometallic complex of which the chemical formula comprises at least two different metal atoms M and M', M being an atom chosen from the group consisting of the atoms of columns 2 and 13 of the periodic table and M' being an atom chose from the group consisting of the atoms of column 4 of the periodic table, and at least one alkoxide or chelating ligand.

19 Claims, No Drawings

SILICONE COMPOSITION THAT CAN BE CURED IN THE PRESENCE OF WATER OR ATMOSPHERIC MOISTURE

CROSS REFERENCE TO RELATED APPLICATIONS

This application is a §371 National Stage Application of PCT/FR2014/053141, filed 3 Dec. 2014, which claims priority to FR 13/62008, filed 3 Dec. 2013.

BACKGROUND

Field of the Invention

The present invention relates to a novel composition that can be cured in the presence of water or atmospheric moisture, preferably at room temperature, commonly called RTV silicone (for "Room Temperature Vulcanizable"). More specifically, the invention relates to a composition that can be cured in the presence of water or atmospheric moisture comprising at least one polyorganosiloxane A having one or more condensable or hydrolyzable and condensable group(s) and at least one compound C that is a heterometallic complex, making it unnecessary to use a tin-based catalyst.

DESCRIPTION OF RELATED ART

The formulations of silicones that are preferably curable at room temperature (or RTV silicones) are manufactured in large tonnages and are used for making mastics, seals, moldings, glues, foams etc. Classically, these formulations contain a hydroxyl-terminated silicone oil, for example an α,ω-(hydroxydimethylsilyl)-polydimethylsiloxane, optionally prefunctionalized with a silane so that it has hydrolyzable and condensable ends, a crosslinking agent, a polycondensation catalyst, classically a tin salt or an alkyl titanate, and optionally various fillers and additives depending on the intended final application.

These silicone compositions that harden by polymerization and/or crosslinking at ambient temperature (which can vary between 5° and 30° C. depending on the region) are familiar to a person skilled in the art and are classified in two separate groups:

compositions packaged as a "single-component" composition (RTV-1), which are in the form of a single part (or component) in airtight packaging, and compositions packaged as a "two-component" composition (RTV-2), which are in the form of two separate parts (hence the designation "two-component") and whose packaging containing the catalyst is airtight.

The purpose of the airtight packaging is to prevent the silicone compositions containing the catalyst from coming into contact with atmospheric moisture during storage before use. During curing, which takes place by polymerization and/or crosslinking of these silicone compositions, water is supplied by atmospheric moisture in the case of the RTV-1s. In the case of the RTV-2s, dimethyltin dicarboxylates are commonly used as catalysts, but they may require the addition of some water to one of the parts in order to activate the catalyst and enable the polycondensation reaction when the contents of the two parts are mixed with ambient air so as to form the elastomer network, which leads to curing of the composition.

For example, the single-component silicone compositions (RTV-1) used as mastics or adhesives undergo cold crosslinking by a Mechanism involving a certain number of reactions, which may be successive or simultaneous:

A functionalization reaction, resulting from bringing a silicone oil having silanol functions, for example a hydroxyl-terminated silicone oil, such as an α,ω-(hydroxydimethylsilyl)-polydimethylsiloxane, into contact with a crosslinking agent, such as a silane of the type $SiX_4$ (for example a silicate) or a compound having the following function —$SiX_3$ with X most often being an alkoxy, acyloxy, amino, amido, enoxy, aminoxy, ketiminoxy or oxime function. These functions are well known as being reactive with silanol functions. The resulting product is most often called "functionalized oil". This reaction may be desired directly during preparation of the composition (functionalization in situ) or optionally as a preliminary step before adding the other components of the composition. In this preliminary step, it is common to use a functionalization catalyst such as lithia (or lithium hydroxide) or potash in order to endow the single-component composition with good stability in storage. For this purpose, a person skilled in the art will be able to select specific functionalization catalysts and will adjust the amount of the reactants so as to have a molar excess of crosslinking agent relative to the silanol functions to be functionalized.

Crosslinking by hydrolysis of the functionalized oil generally due to water vapor that diffuses into the material from the surface exposed to the atmosphere, and condensation between the silanol groups formed and other residual reactive functions.

With regard to the compositions packaged in the form of a two-component composition (RTV-2), the first component (or part) comprises the polycondensable polyorganosiloxanes and the second component, which is airtight, contains the catalyst and one or more crosslinking agents. The two components (or parts) are mixed at the time of use and the mixture hardens by crosslinking reactions in the form of a relatively hard elastomer, notably when the composition comprises reinforcing fillers. These compositions packaged in two-component systems are well known and are notably described in the work of Walter Noll "Chemistry and Technology of Silicones" 1968, 2nd edition, pages 395 to 398. These compositions most often comprise the following ingredients:

a reactive polyorganosiloxane with silanol groups at the end of the chain (for example an am-di(hydroxydimethylsilyl)(polydimethylsiloxane), in the chain, or both at the end of the chain and in the chain;

a crosslinking agent;

a condensation catalyst; and optionally water, often present when a dialkyltin dicarboxylate is used as catalyst, the water serving as activator for said catalyst.

The best known catalysts, which have been used for decades in both single-component and two-component compositions, are tin derivatives. We may notably mention the compounds based on alkyltin, such as dibutyltin dilaurate (DBTDL), which are known to be good crosslinking catalysts while liquid, soluble in silicone oils, and colorless. However, they have the drawback of being toxic and classified CMR II, toxic for reproduction. Replacement of tin-based catalysts currently represents a major challenge for the actors in this field of technology.

Alternative catalysts have already been proposed in the prior art, notably titanium-based catalysts (see for example international patent application WO 2013/036546). A great many other catalysts have been mentioned, for example catalysts based on zinc, scandium, ytterbium, copper, silver, cerium, molybdenum, bismuth, hafnium or guanidine derivatives. The use of chelates of zirconium or of titanium is described in particular in international patent application WO 01/49789. Moreover, in patent application FR 2 856 694 it was proposed to use mixed catalysts consisting of a combination of at least two metal derivatives, the first being a derivative of titanium or zirconium, and the second being a derivative of zinc, aluminum, boron or bismuth. The mixed catalysts are obtained simply by combining several monometallic catalysts at the time of formulation. Even if interesting effects are obtained, in particular in terms of yellowing and adherence, these metal catalysts cannot give the crosslinking kinetics and the hardnesses of the elastomers obtained with tin-based catalysts.

In this context, one of the aims of the present invention is to propose novel nontoxic condensation catalysts to replace the tin-based catalysts. These catalysts may advantageously have one or more of the following properties:
be equivalent to or have better performance from the standpoint of kinetics than tin-based catalysts;
allow curing of the elastomers that is equivalent to or better than that obtained with tin-based catalysts;
lead to translucent materials, which do not yellow over time;
retain its performance in the absence or in the presence of an adhesion promoter.

SUMMARY

The inventors discovered that these aims could be achieved using heterometallic complexes as catalysts of the condensation reaction of polyorganosiloxanes having condensable or hydrolyzable and condensable groups.

According to a first aspect, the invention relates to a composition that can be cured in the presence of water or atmospheric moisture comprising:
(A) at least one polyorganosiloxane A having one or more condensable or hydrolyzable and condensable group(s), and
(B) at least one compound C, capable of catalyzing the condensation reaction of the condensable or hydrolyzable and condensable groups of the polyorganosiloxane A, and which is a heterometallic complex whose chemical formula comprises:
at least two different metal atoms M and M', M being an atom selected from the group consisting of the atoms in columns 2 and 13 of the periodic table and M' being an atom selected from the group consisting of the atoms in column 4 of the periodic table, and
at least one alkoxide ligand or chelating ligand.

According to another aspect, the invention relates to the use of a compound C as defined above in the present description, as catalyst of a condensation reaction of a polyorganosiloxane having one or more condensable or hydrolyzable and condensable group(s).

In particular, the invention also relates to the use of a heterometallic complex according to the invention as described in the present description as polycondensation catalyst of a polyorganosiloxane curable by a polycondensation reaction to form a silicone elastomer.

Moreover, the present invention also relates to a heterometallic chelated complex whose chemical formula comprises:
at least two different metal atoms M and M', M being an atom selected from the group consisting of the atoms in columns 2 and 13 of the periodic table and M' being an atom selected from the group consisting of the atoms in column 4 of the periodic table, and
at least one chelating ligand of general formula (I):

in which:
each X represents, independently of one another, an oxygen atom or a group NR', R' representing a $C_1$ to $C_8$ alkyl group, optionally substituted one or more times with a halogen atom and/or with an aryl group;
$R^1$ and $R^2$, independently of one another, represent:
a $C_1$ to $C_8$ alkyl or cycloalkyl group, optionally substituted one or more times with a halogen atom and/or with an aryl group,
an aryl group, optionally substituted one or more times with a halogen atom,
a $C_1$ to $C_8$ alkoxide group, optionally substituted one or more times with a halogen atom and/or with an aryl group,
—OH,
—NR"2, each R" representing, independently of one another, a hydrogen atom or a $C_1$ to $C_8$ alkyl group, optionally substituted one or more times with a halogen atom and/or with an aryl group;
$R^3$ represents a monovalent group, preferably a hydrogen atom or a $C_1$ to $C_4$ alkyl group.

DETAILED DESCRIPTION OF A PREFERRED EMBODIMENT

It is to be understood that, in the context of this description, the term "between" must be interpreted as including the limits indicated.

The composition according to the invention is a composition that is curable (also called "vulcanizable") in the presence of water or atmospheric moisture, commonly called RTV silicone. Conventionally it comprises:
at least one polyorganosiloxane A having one or more condensable or hydrolyzable and condensable group (s), and
at least one compound C according to the invention capable of catalyzing the condensation reaction of the condensable or hydrolyzable and condensable groups of the polyorganosiloxane A.

Said composition is curable in the presence of water or atmospheric moisture preferably at room temperature. "Room temperature" preferably means about 20° C.

Said compound C is a heterometallic complex whose chemical formula comprises:
at least two different metal atoms M and M', M being an atom selected from the group consisting of the atoms in columns 2 and 13 of the periodic table and M' being an atom selected from the group consisting of the atoms in column 4 of the periodic table, and
at least one alkoxide ligand or chelating ligand.

In the present invention, the atoms in columns 2 and 13 of the periodic table are beryllium (Be), magnesium (Mg), calcium (Ca), strontium (Sr), barium (Ba), radium (Ra), boron (B), aluminum (Al), gallium (Ga), indium (In) and thallium (Tl). Preferably, M is an atom of magnesium or of aluminum. The atoms in column 4 of the periodic table are titanium (Ti), zirconium (Zr), hafnium (Hf) and rutherfordium (Rf). Preferably, M' is a titanium or zirconium atom.

In the present invention, the expression "heterometallic complex" denotes a polynuclear complex whose chemical formula comprises at least two different metal atoms. According to a preferred embodiment, compound C is a heterometallic complex whose chemical formula comprises:
- at least two different metal atoms M and M', M being an atom of magnesium (Mg) or of aluminum (Al), and preferably an aluminum atom (Al), and M' being an atom of titanium (Ti) or of zirconium (Zr), and
- at least one alkoxide ligand or chelating ligand.

It may therefore preferably be selected from the group consisting of the heterometallic complexes whose chemical formula comprises at least one alkoxide ligand or chelating ligand and at least two different metal atoms M and M' selected from the following pairs:
- M is a magnesium atom (Mg) and M' is a titanium atom (Ti),
- M is a magnesium atom (Mg) and M' is a zirconium atom (Zr),
- M is an aluminum atom (Al) and M' is a titanium atom (Ti), or
- M is an aluminum atom (Al) and M' is a zirconium atom (Zr).

Even more preferably it is selected from the group consisting of the heterometallic complexes whose chemical formula comprises at least one alkoxide ligand or chelating ligand and at least two different metal atoms M and M' selected from the following pairs:
- M is an aluminum atom (Al) and M' is a titanium atom (Ti), or
- M is an aluminum atom (Al) and M' is a zirconium atom (Zr).

Even more preferably, compound C according to the invention is selected from the group consisting of the heterometallic complexes whose chemical formula comprises at least one alkoxide ligand or chelating ligand and at least two metal atoms M and M', M being an aluminum atom (Al) and M' a zirconium atom (Zr).

The molar ratio of metal M to metal M' may be between 0.1 and 10, and preferably between 0.25 and 4.

According to a much preferred embodiment, compound C according to the invention is selected from the group consisting of:
- the heterometallic complexes whose chemical formula comprises at least one alkoxide ligand or chelating ligand and at least two different metal atoms M and M', M being an aluminum atom and M' being a zirconium atom and in which the molar ratio Al/Zr has a value of 1;
- the heterometallic complexes whose chemical formula comprises at least one alkoxide ligand or chelating ligand and at least two different metal atoms M and M', M being an aluminum atom and M' being a zirconium atom and in which the molar ratio Al/Zr has a value of 2;
- the heterometallic complexes whose chemical formula comprises at least one alkoxide ligand or chelating ligand and at least two different metal atoms M and M', M being an aluminum atom and M' being a titanium atom and in which the molar ratio Al/Ti has a value of 1;
- the heterometallic complexes whose chemical formula comprises at least one alkoxide ligand or chelating ligand and at least two different metal atoms M and M', M being an aluminum atom and M' being a titanium atom and in which the molar ratio Al/Ti has a value of 2;
- the heterometallic complexes whose chemical formula comprises at least one alkoxide ligand or chelating ligand and at least two different metal atoms M and M', M being a magnesium atom and M' being a zirconium atom and in which the molar ratio Mg/Zr has a value of 1;
- the heterometallic complexes whose chemical formula comprises at least one alkoxide ligand or chelating ligand and at least two different metal atoms M and M', M being a magnesium atom and M' being a titanium atom and in which the molar ratio Mg/Ti has a value of 1.

According to an even more preferred embodiment, compound C is selected from the group consisting of:
- the heterometallic complexes whose chemical formula comprises:
  - at least two different metal atoms M and M', M being aluminum and M' being zirconium and in which the molar ratio Al/Zr=0.5, 1 or 2; and
  - at least one alkoxide ligand or chelating ligand; and
- the heterometallic complexes whose chemical formula comprises:
  - at least two different metal atoms M and M', M being aluminum and M' being titanium and in which the molar ratio Al/Ti=1 or 2, and
  - at least one alkoxide ligand or chelating ligand.

One or more ligands will complex the metal atoms. The heterometallic complex according to the invention comprises at least one ligand selected from an alkoxide ligand or a chelating ligand.

The expression "alkoxide ligand" denotes a ligand of chemical formula OR, R representing a $C_1$ to $C_{24}$ alkyl group. Preferably, the alkoxide ligand is a ligand of chemical formula OR, R representing a $C_2$ to $C_{12}$ alkyl group, and more preferably, R is selected from the group consisting of ethyl, isopropyl, n-propyl, n-butyl, sec-butyl, tert-butyl, isobutyl, 2-ethylhexyl and 2-butyloctyl.

The expression "chelating ligand" denotes a ligand bound at least twice to one or more metal atoms. The chelating ligand may be selected from the bidentate, tridentate or tetradentate chelating ligands, preferably bidentate. A large number of chelating ligands are known to a person skilled in the art.

Hereinafter, the chelating ligands are described in their neutral, free form. When they are associated with a central element in a complex, it is possible that these chelating ligands have lost a proton or are in a tautomeric form.

Preferably, the chelating ligand is a ligand of general formula (I):

(I)

in which:
- each X represents, independently of one another, an oxygen atom or a group NR', R' representing a $C_1$ to $C_8$ alkyl group, optionally substituted one or more times with a halogen atom and/or with an aryl group;

R¹ and R², independently of one another, represent:
- a $C_1$ to $C_8$ alkyl or cycloalkyl group, optionally substituted one or more times with a halogen atom and/or with an aryl group,
- an aryl group, optionally substituted one or more times with a halogen atom,
- a $C_1$ to $C_8$ alkoxide group, optionally substituted one or more times with a halogen atom and/or with an aryl group,
- —OH,
- —NR"2, each R" representing, independently of one another, a hydrogen atom or a $C_1$ to $C_8$ alkyl group, optionally substituted one or more times with a halogen atom and/or with an aryl group;

R³ represents a monovalent group, preferably a hydrogen atom or a $C_1$ to $C_4$ alkyl group.

Preferably, the chelating ligand is selected from the group consisting of a ligand of the β-keto-ester type, a ligand of the β-diester type, a ligand of the β-diketone type, a ligand of the β-diacid type, a ligand of the β-ketoamide type and a ligand of the β-diimide type.

Even more preferably, the chelating ligand is selected from the group consisting of ethyl acetoacetate, ethyl ethyl acetate, propionyl ethyl acetate, 2-ethyl ethyl acetoacetate, trifluoroethyl acetoacetate, t-butyl ethyl acetatoacetate, cyclopropyl ethyl acetoacetate, propyl acetoacetonate, acetoketone, hexafluoroacetylacetone, 4,4,4-trifluoro-1-phenyl-1,3-butanedione, 1,3-diphenyl-1,3-propanedione, 2,2,6,6-tetramethyl-3,5-heptanedione, diisopropyl malonate, acetoacetamide, bis-N,N'-(2-phenylethyl)-2,4-diiminopentane, methyl acrylate, 1,8-diazabicyclo(5.4.0)undec-7-ene and pivaloyl methyl acetate.

The heterometallic complex may comprise a single ligand or several ligands. The number and nature of the ligands is adapted to the coordination number of the metal atoms. When the heterometallic complex only comprises a single ligand, the latter is selected from an alkoxide ligand and a chelating ligand as defined above. When the heterometallic complex comprises several ligands, the latter may be identical or different. There may be for example several identical or different alkoxide ligands, several identical or different chelating ligands, or a mixture of alkoxide ligand(s) and chelating ligand(s).

Moreover, other types of ligands may be present.

Quite particularly, the heterometallic complex may comprise one or more oxo ligands (O), one or more hydroxyl ligands (OH) and/or one or more alcohol ligands. These ligands are likely to be present notably owing to the phenomena of oligomerization and of hydrolysis of the metal complexes with alkoxide ligands. The expression "alcohol ligand" denotes a ligand of chemical formula ($C_1$-$C_{24}$ alkyl)-OH.

Moreover, the heterometallic complex may comprise other neutral ligands. The expression "neutral ligand" denotes, in the present invention, a ligand that coordinates the metal by supplying a pair of electrons to the latter. A person skilled in the art will use any type of neutral ligand suitable for the metal in question. The neutral ligand may be selected from the neutral ligands bearing at least one pair of free electrons such as amines, phosphines, ethers and water, the ligands being coordinated via one or more π bonds such as ethylene, and the ligands being coordinated via a σ bond such as $H_2$. Preferably, the heterometallic complex according to the invention does not comprise any other neutral ligand.

Compound C according to the invention may be a heterometallic complex of general formula (II):

in which:
- the symbol M represents an atom of magnesium Mg or of aluminum Al;
- the symbol M' represents an atom of titanium Ti or of zirconium Zr;
- the symbol Lig1 represents an alkoxide ligand;
- the symbol Lig2 represents a chelating ligand;
- the symbol Lig3 represents a ligand selected from the group consisting of: an oxo ligand, a hydroxide ligand, an alcohol ligand and a neutral ligand; and
- m, n, x, y and z are numbers such that m>0, n>0, x≥0, y≥0, z≥0 and (x+y)>0.

In the above notation, the numbers m, n, x, y and z may or may not be integers. When they are not integers, a person skilled in the art will understand that formula (II) is a general formula based on the composition of the complex and on the molar ratios between the different atoms or groups of atoms. Moreover, it is understood in this formula that if x is different from zero, then one or more ligands Lig1, which may be identical or different, may be present, if y is different from zero, then one or more ligands Lig2, which may be identical or different, may be present, and if z is different from zero, then one or more ligands Lig3, which may be identical or different, may be present.

The numbers m and n may be selected independently from between 0 and 20, zero being excluded, and the ratio m/n may be between 0.1 and 10. Preferably, m and n may independently be equal to 1, 2, 3 or 4. Moreover, the ratio m/n is preferably between 0.25 and 4.

Compound C according to the invention may notably be selected from the group consisting of the heterometallic complexes of formulas (IIa) to (IIf):

in which Lig1, Lig2, Lig3, x, y and z are as defined above.

The heterometallic complex according to the invention comprises at least one alkoxide ligand Lig1 or chelating ligand Lig2. In general formula (II), x, y and z are numbers such that x≥0, y≥0, z≥0 and (x+y)>0. x and y therefore cannot be equal to zero at the same time. x may preferably be between 0 and 20, and more preferably between 0.1 and 12. y may preferably be between 0 and 20, and more preferably between 2 and 10. z may preferably be between 0 and 2. Lig1 is an alkoxide ligand, preferably as described above, Lig2 is a chelating ligand, preferably as described above, and Lig3 is a neutral ligand, preferably as described above.

Two particularly preferred embodiments are presented below.

According to a first especially preferred embodiment of the present invention, compound C is a heterometallic alkoxide complex whose chemical formula comprises at least two different metal atoms M and M', M being a magnesium or aluminum atom and M' being a titanium or zirconium atom. This complex comprises at least one alkoxide ligand as defined above.

The ligands of this complex may be only alkoxides, which may be identical or different, optionally mixed with one or more ligands selected from the group consisting of an oxo ligand, a hydroxide ligand and an alcohol ligand.

Compound C according to this embodiment may be a heterometallic complex of general formula (II) in which "y" has a value of zero and "x" is different from zero. Preferably it is a heterometallic alkoxide complex of general formula (III):

$$[M_mM'_n(Lig1)_x(Lig3)_z] \quad\quad (III)$$

in which:
the symbol M represents an atom of magnesium Mg or of aluminum Al;
the symbol M' represents an atom of titanium Ti or of zirconium Zr;
the symbol Lig1 represents an alkoxide ligand;
the symbol Lig3 represents a ligand selected from the group consisting of an oxo ligand, a hydroxide ligand and an alcohol ligand;
m, n, x, y and z are numbers such that m>0, n>0, x>0 and z≥0.

In particular, compound C is a heterometallic alkoxide complex whose chemical formula comprises:
at least two different metal atoms M and M', M being magnesium or aluminum and M' being titanium or zirconium, and
at least one alkoxide ligand;
and preferably said heterometallic alkoxide complex is selected from the group consisting of:
the heterometallic alkoxide complexes whose chemical formula comprises:
at least two different metal atoms M and M', M being aluminum and M' being zirconium,
at least one alkoxide ligand of chemical formula O-(linear or branched $C_3$ to $C_{12}$ alkyl), and
in which the molar ratio Al/Zr has the value 0.5, 1 or 2;
the heterometallic alkoxide complexes whose chemical formula comprises:
at least two different metal atoms M and M', M being magnesium and M' being zirconium,
at least one alkoxide ligand of chemical formula O-(linear or branched $C_2$ to $C_{12}$ alkyl), and
in which the molar ratio Mg/Zr has the value 0.5, 1, 2, 3 or 4; and
the heterometallic alkoxide complexes whose chemical formula comprises:
at least two different metal atoms M and M', M being aluminum and M' being titanium,
at least one alkoxide ligand of chemical formula O-(linear or branched $C_3$ to $C_{12}$ alkyl), and
in which the molar ratio Al/Ti has a value of 1 or 2;
and even more preferably said heterometallic alkoxide complex is selected from the group consisting of $AlZr(OBu)_4(OsBu)_3$, $Al_2Zr(OnBu)_4(OsBu)_6$, $AlZr_2(OnBu)_{11}$, $AlTi(OsBu)_3(OnBu)_4$ and $Al_2Ti(OnBu)_{10}$.

Certain heterometallic alkoxide complexes according to this embodiment are commercially available. For example, the company Gelest supplies aluminum-titanium, aluminum-zirconium and magnesium-zirconium heterometallic alkoxide complexes.

Moreover, the heterometallic alkoxide complexes according to this embodiment may be prepared from the corresponding monometallic alkoxides. A possible synthesis route consists of reacting the monometallic alkoxides together, with stirring, preferably without solvent and preferably at room temperature, for a sufficient time for the association reaction to take place. This reaction is generally exothermic.

The desired heterometallic alkoxide complexes may be obtained conventionally by ligand exchange. Exchange of alkoxide ligands may be performed conventionally by reacting a first complex with the alcohol corresponding to the desired alkoxide ligand, this alcohol being less volatile than the alcohol corresponding to the ligand of the first complex, optionally in a suitable solvent, with heating and preferably under reduced pressure.

According to a second especially preferred embodiment of the present invention, compound C is a heterometallic chelated complex whose chemical formula comprises at least two different metal atoms M and M', M being a magnesium or aluminum atom and M' being a titanium or zirconium atom. This complex comprises at least one chelating ligand as defined above.

The ligands of this complex may be chelates only, which may be identical or different, or else one or more chelates mixed with one or more ligands selected from the group consisting of an alkoxide ligand, an oxo ligand, a hydroxide ligand and an alcohol ligand.

Compound C according to this embodiment may be a heterometallic complex of general formula (II) in which "y" is different from zero. It is preferably a heterometallic chelated complex of general formula (IV):

$$[M_mM'_n(Lig1)_x(Lig2)_y(Lig3)_z] \quad\quad (IV)$$

in which:
the symbol M represents an atom of magnesium Mg or of aluminum Al;
the symbol M' represents an atom of titanium Ti or of zirconium Zr;
the symbol Lig1 represents an alkoxide ligand;
the symbol Lig2 represents a chelating ligand;
the symbol Lig3 represents a ligand selected from the group consisting of an oxo ligand, a hydroxide ligand and an alcohol ligand;
m, n, x, y and z are numbers such that m>0, n>0, x≥0, y>0 and z>0.

In particular, compound C is a heterometallic chelated complex whose chemical formula comprises:
at least two different metal atoms M and M', M being magnesium or aluminum and M' being titanium or zirconium, and
at least one chelate ligand;
said heterometallic chelated complex preferably being selected from the group consisting of:
the heterometallic chelated complexes whose chemical formula comprises:
at least two different metal atoms M and M', M being aluminum and M' being zirconium,
at least one chelating ligand, preferably selected from the group consisting of ethyl acetoacetate, propyl acetoacetate and diisopropyl malonate,
optionally at least one alkoxide ligand of chemical formula O-(linear or branched $C_3$ or $C_4$ alkyl), and
having a molar ratio Al/Zr=1 or 2;
the heterometallic chelated complexes whose chemical formula comprises:
at least two different metal atoms M and M', M being aluminum and M' being zirconium, at least one chelating ligand, preferably selected from the group consisting of ethyl acetoacetate, propyl acetoacetate and diisopropyl malonate,
having a molar ratio Al/Zr=1 or 2, and
not comprising an alkoxide ligand;
the heterometallic chelated complexes whose chemical formula comprises:
at least two different metal atoms M and M', M being magnesium and M' being zirconium,
at least one chelating ligand, preferably ethyl acetoacetate, and
having a molar ratio Mg/Zr=1;
the heterometallic chelated complexes whose chemical formula comprises:
at least two different metal atoms M and M', M being aluminum and M' being titanium,
at least one chelating ligand, preferably selected from the group consisting of ethyl acetoacetate and propyl acetoacetate,
optionally at least one alkoxide ligand of chemical formula O-(linear or branched $C_3$ or $C_4$ alkyl), and
having a molar ratio Al/Ti=1; and
the heterometallic chelated complexes whose chemical formula comprises:
at least two different metal atoms M and M', M being magnesium and M' being titanium,
at least one chelating ligand, preferably ethyl acetoacetate,
optionally at least one alkoxide ligand of chemical formula O-(linear or branched $C_3$ alkyl), and
having a molar ratio Mg/Ti=1;
and even more preferably said heterometallic chelated complex being selected from the group consisting of AlZr(EAA)$_3$(OnPr)$_4$, Al$_2$Zr(EAA)$_6$(OnPr)$_4$, AlZr(EAA)$_7$, Al$_2$Zr(EAA)$_{10}$ and AlTi(EAA)$_3$(OnBu)$_4$.

Certain monometallic chelated complexes are commercially available. For example, the company DuPont offers chelated complexes of titanium or of zirconium under the name Tyzor®.

Other monometallic chelated complexes possessing the desired ligands may be obtained conventionally by ligand exchange. Ligand exchange may be performed conventionally by reacting a first complex with the precursor corresponding to the desired ligand, optionally in a suitable solvent, with heating and preferably under reduced pressure.

Synthesis of the heterometallic chelated complexes may be carried out by three methods:
By a Lewis acid-base reaction by contacting one or more alkoxide complexes and/or monometallic chelates, preferably at room temperature and without solvent, for a sufficient time for the association reaction to take place, for example according to the following reaction scheme:

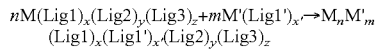

in which M, M', Lig1, Lig2, Lig3, n, m, x, y and z have the meanings given above, Lig1' represents an alkoxide ligand identical to or different from Lig1, x' is a number such that x'>0;
By substitution of one or more alkoxide ligands on a heterometallic alkoxide complex by a chelate ligand, for example according to the following reaction scheme:

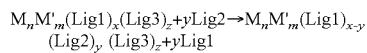

in which M, M', Lig1, Lig2, Lig3, n, m, x, y and z have the meanings given above;
By synthesis in two steps:
a) synthesis of a monometallic chelated complex starting from a monometallic alkoxide complex by ligand exchange with a chelate, for example according to the following reaction scheme:

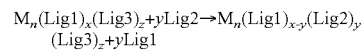

b) and then association of the monometallic chelated complex with a monometallic alkoxide complex based on a different metal, for example according to the following reaction scheme:

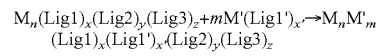

This two-step synthesis route may advantageously be one-pot, without isolation of the intermediates.

As far as the inventors know, no heterometallic chelated complex as described in the present invention has been proposed in the past.

That is why the present invention also relates to a heterometallic chelated complex comprising:
at least two different metal atoms M and M', M being a magnesium or aluminum atom and M' being a titanium or zirconium atom, and
at least one chelate ligand.

The inventors discovered, quite unexpectedly, that the heterometallic complexes according to the invention were better catalysts of the condensation reaction of the condensable or hydrolyzable and condensable groups of a polyorganosiloxane, and in particular of the polycondensation reaction of the silicones, than the simple mixture of the corresponding monometallic complexes.

Compound C is present as catalyst in the composition that can be cured in the presence of water or atmospheric moisture according to the invention in a catalytic amount. The concentration of catalyst in the composition according to the invention may be between 0.1% and 6%, preferably between 1% and 3%, by weight, relative to the total weight of the composition.

Preferably, the polyorganosiloxane A according to the invention bears at least two groups selected from the group consisting of the hydroxyl, alkoxy, alkoxy-alkylene-oxy, amino, amido, acylamino, aminoxy, iminoxy, ketiminoxy, acyloxy and enoxy groups.

According to a preferred embodiment, the polyorganosiloxane A comprises:
(i) at least two siloxyl units of the following formula (V):

in which:
the symbols $R^4$, which may be identical or different, represent monovalent $C_1$ to $C_{30}$ hydrocarbon radicals,
the symbols Z, which may be identical or different, each represent a hydrolyzable and condensable group or a hydroxyl group, and preferably are selected from the group consisting of the hydroxyl, alkoxy, alkoxy-alkylene-oxy, amino, amido, acylamino, aminoxy, iminoxy, ketiminoxy, acyloxy, iminoxy, ketiminoxy and enoxy groups,
a is equal to 0, 1 or 2, b is equal to 1, 2 or 3, the sum a+b is equal to 1, 2 or 3, and (ii) optionally one or more siloxyl unit(s) of the following formula (VI):

$$R^c_5 SiO_{\frac{4-c}{2}} \quad (VI)$$

in which:
the symbols $R^5$, which may be identical or different, represent monovalent $C_1$ to $C_{30}$ hydrocarbon radicals optionally substituted with one or more halogen atoms or with amino, ether, ester, epoxy, mercapto or cyano groups, and
the symbol c is equal to 0, 1, 2 or 3.

Preferably, the polyorganosiloxane A has the general formula (VII):

$$Z_d R^6_{3-d} Si—O—(SiR^6_2—O)_p—SiR^6_{3-d} Z_d \quad (VII)$$

in which:
the symbols Z, which may be identical or different, each represent a hydrolyzable and condensable group or a hydroxyl group, and preferably are selected from the group consisting of the hydroxyl, alkoxy, alkoxy-alkylene-oxy, amino, amido, acylamino, aminoxy, iminoxy, ketiminoxy, acyloxy and enoxy groups,
the symbols $R^6$, which may be identical or different, represent monovalent $C_1$ to $C_{30}$ hydrocarbon radicals optionally substituted with one or more halogen atoms or with amino, ether, ester, epoxy, mercapto or cyano groups,
the symbol d is equal to 1, 2 or 3, preferably equal to 2 or 3, and when Z is a hydroxyl group, then d=1,
when the polyorganosiloxane A is a silicone oil, the symbol p is between 1 and 2000, preferably between 1 and 1000, and when the polyorganosiloxane A is a silicone gum, the symbol p is preferably greater than 2000 and its value is determined in such a way that the consistency of the gum is between 200 and 2000 according to the standard or standards mentioned in the present description.

In formulas (V), (VI) and (VII), the symbols $R^4$, $R^5$ and $R^6$ are preferably:
alkyl radicals having from 1 to 20 carbon atoms, optionally substituted with one or more aryl or cycloalkyl groups, with one or more halogen atoms or with amino, ether, ester, epoxy, mercapto, cyano or (poly)glycol groups. We may mention for example the methyl, ethyl, propyl, isopropyl, butyl, pentyl, hexyl, ethyl-2-hexyl, octyl, decyl, trifluoro-3,3,3-propyl, trifluoro-4,4,4-butyl, pentafluoro-4,4,4,3,3-butyl radicals;
cycloalkyl and halocycloalkyl radicals having from 5 to 13 carbon atoms such as the cyclopentyl, cyclohexyl, methylcyclohexyl, propylcyclohexyl, difluoro-2,3-cyclobutyl, difluoro-3,4-methyl-5-cycloheptyl radicals;
mononuclear aryl and haloaryl radicals having from 6 to 13 carbon atoms such as the radicals: phenyl, tolyl, xylyl, chlorophenyl, dichlorophenyl, trichlorophenyl; or
alkenyl radicals having from 2 to 8 carbon atoms such as the radicals: vinyl, allyl and butene-2-yl.

The viscosity of the polyorganosiloxane A is generally between 50 mPa·s and 1 000 000 mPa·s at 25° C. When it is a silicone gum, the viscosity of the polyorganosiloxane A is then above 1 000 000 mPa·s at 25° C. and then the consistency of the gum is preferably between 200 and 2000. The consistency may be determined by measuring the penetrability using a penetrometer for example according to one of the AFNOR standards NFT 60 119 or NFT 60 123. Standard NFT 60 123 is particularly suitable for the present description.

In the particular case when the polyorganosiloxane A is a polyorganosiloxane of general formula (VII) with symbols Z of the hydroxyl type, then the symbol d will preferably be equal to 1. In this case it is preferable to use poly(dimethylsiloxane)s having silanol functions in terminal positions (also called "alpha-omega" positions) and which are generally oils whose viscosity varies for example for a molding application from 100 mPa·s at 25° C. to 20 000 mPa·s at 25° C. It is advantageous to use those for which at least 60% of the radicals $R^4$ and $R^5$ (in formulas (V) and (VI)) or radical $R^6$ (in formula (VII)) are methyl radicals, the other radicals generally being phenyl and/or vinyl radicals.

According to the invention, the symbols Z each represent a hydroxyl group or a hydrolyzable and condensable group, preferably selected from the group consisting of the alkoxy, alkoxy-alkylene-oxy, amino, amido, acylamino, aminoxy, iminoxy, ketiminoxy, acyloxy and enoxy groups.

When the polyorganosiloxane A has hydrolyzable and condensable groups Z according to the invention and is a polyorganosiloxane, preferably a polydimethylsiloxane with hydrolyzable and condensable groups Z, most often it is described as a functionalized polymer and it corresponds to a form that is stable in the absence of humidity, which may be used in a single-component composition and thus be packaged in sealed cartridges, which will be opened by the operator at the time of use to form a cured elastomer after curing.

As examples of hydrolyzable and condensable groups Z of the alkoxy type, we may mention the groups having from 1 to 8 carbon atoms such as the methoxy, ethoxy, n-propoxy, isopropoxy, n-butoxy, iso-butoxy, sec-butoxy, tert-butoxy, 2-methoxyethoxy, hexyloxy or octyloxy groups.

As an example of hydrolyzable and condensable groups Z of the alkoxy-alkylene-oxy type, we may mention the methoxy-ethylene-oxy group.

As examples of hydrolyzable and condensable groups Z of the amino type, we may mention the methylamino, dimethylamino, ethylamino, diethylamino, n-butylamino, sec-butylamino or cyclohexylamino groups.

As an example of hydrolyzable and condensable groups Z of the amido type, we may mention the N-methyl-acetamido group.

As an example of hydrolyzable and condensable groups Z of the acylamino type, we may mention the benzoyl-amino group.

As examples of hydrolyzable and condensable groups Z of the aminoxy type, we may mention the dimethylaminoxy, diethylaminoxy, dioctylaminoxy or diphenylaminoxy groups.

As examples of hydrolyzable and condensable groups Z of the iminoxy and in particular ketiminoxy type, we may mention the groups derived from the following oximes: acetophenone-oxime, acetone-oxime, benzophenone-oxime, methyl-ethyl-ketoxime, diisopropylketoxyme or methyl-isobutyl-ketoxime.

As an example of hydrolyzable and condensable groups Z of the acyloxy type, we may mention the acetoxy group.

As an example of hydrolyzable and condensable groups Z of the enoxy type, we may mention the 2-propenoxy group.

When the polyorganosiloxane A has groups Z of the hydroxyl type, they may then be functionalized in situ in the single-component compositions, via a functionalization catalyst, so as to be able to store them and package them in sealed cartridges. Preferably, the functionalization catalyst is lithia (or lithium hydroxide) or potash. Lithia is widely available commercially. Preferably, it is used in solution in an alcohol, for example methanol or ethanol. Preparation of polyorganosiloxane A comprising groups alkoxylated by functionalization is described for example in French patent application FR 2 638 752.

Preferably, the polyorganosiloxane A has the formula (VIII):

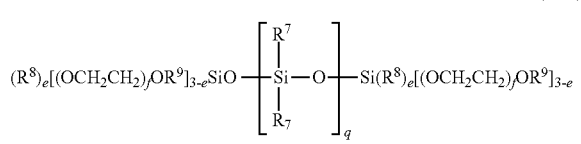

in which:
the substituents $R^7$, which may be identical or different, each represent a monovalent $C_1$ to $C_{13}$ hydrocarbon radical, saturated or unsaturated, substituted or unsubstituted, aliphatic, cyclane or aromatic;
the substituents $R^8$, which may be identical or different, each represent a monovalent saturated or unsaturated $C_1$ to $C_{13}$ hydrocarbon radical, substituted or unsubstituted, aliphatic, cyclane or aromatic;
the substituents $R^9$, which may be identical or different, each represent a linear or branched $C_1$ to $C_6$ alkyl radical;
q has a sufficient value to endow the polyorganosiloxane A with a dynamic viscosity at 25° C. in the range from 50 mPa·s to 1 000 000 mPa·s when it is a silicone oil or above 1 000 000 mPa·s when it is a gum, and preferably when it is a silicone oil, the symbol q is between 1 and 2000, and preferably between 1 and 1000, and when it is a silicone gum, q is preferably greater than 2000 and its value will be determined in such a way that the consistency of the gum is between 200 and 2000 according to the standard or standards mentioned in the present description; and
the subscript e is equal to zero or 1 and the subscript f is equal to zero or 1.

According to another preferred embodiment, the polyorganosiloxane A comprising at least one alkoxylated group is obtained by reacting, optionally in situ, in the presence of a catalytically effective amount of at least one functionalization catalyst:
a) at least one polyorganosiloxane A' comprising siloxyl units of formula (IX):

in which:
x+y=0, 1, 2 or 3;
the substituents $R^{10}$, which may be identical or different, each represent a monovalent $C_1$-$C_{30}$ hydrocarbon radical, preferably selected from the group consisting of the alkyl, cycloalkyl, aryl, alkaryl and aralkyl radicals, and at least two siloxyl units comprising a group ≡SiOH are present in the polyorganosiloxane A', with
b) at least one polyalkoxylated silane H of formula (X):

in which:
i=0 or 1,
the symbol $R^{11}$ represents a monovalent $C_1$-$C_{13}$ hydrocarbon radical, and
the symbols $R^{12}$, which may be identical or different, each represent a monovalent hydrocarbon $C_1$-$C_6$ radical or an alkoxyalkyl radical optionally having an ester function.

As a preferred constituent, the polyorganosiloxane A comprises the following siloxyl units: $M=[(OH)(R^{13})_2SiO_{1/2}]$ and $D=[R^{14}R^{15}SiO_{2/2}]$; in these formulas $R^{13}$, $R^{14}$ and $R^{15}$ are radicals, which may be identical or different, selected from the group consisting of the linear or branched $C_1$-$C_6$ alkyl radicals (such as methyl, ethyl, propyl, isopropyl, butyl, isobutyl, t-butyl, n-pentyl, n-hexyl), the $C_3$-$C_8$ cycloalkyl radicals (such as cyclopentyl, cyclohexyl), the $C_6$-$C_{10}$ aryl radicals (such as phenyl, naphthyl) and the $C_6$-$C_{15}$ alkarylene radicals (such as tolyls, xylyl).

The polyorganosiloxane A may be a linear polydiorganosiloxane having at least two silanol groups SiOH per molecule and whose dynamic viscosity at 25° C. is between 50 mPa·s and 50×10⁶ mPa·s, preferably between 50 mPa·s and 10⁶ mPa·s in the case of silicone oils, or above 10⁶ mPa·s in the case of silicone gums. All the viscosities considered in the present description correspond to a level of dynamic viscosity that is measured, in a manner known per se, at 25° C. In the case of silicone gums, those may be selected whose consistency is between 200 and 2000.

Preferably, the polyorganosiloxane A is selected from the group consisting of the polyorganosiloxanes of formula (XI):

in which:
r has a sufficient value to endow the polyorganosiloxane of formula (XI) with a dynamic viscosity at 25° C. in the range from 50 mPa·s to 1 000 000 mPa·s when it is a silicone oil or above 1 000 000 mPa·s when it is a silicone gum, and preferably when it is a silicone oil the symbol r is between 1 and 2000, and preferably between 1 and 1000, and when it is a silicone gum, r is preferably greater than 2000 and its value will be determined in such a way that the consistency of the gum is between 200 and 2000 according to the standard or standards mentioned in the present description;
$R^{17}$ and $R^{18}$, which may be identical or different, represent an alkyl having from 1 to 6 carbon atoms, a cycloalkyl having from 3 to 8 carbon atoms, an aryl, an alkarylene or an arallcylene.

The most useful examples of polyorganosiloxane A, owing to their industrial availability, are those for which $R^{17}$ and $R^{18}$ are selected independently from the group of radicals consisting of a methyl, an ethyl, a propyl, an isopropyl, a cyclohexyl, a phenyl, and a 3,3,3-trifluoropropyl. Very preferably, at least about 80% by number of these radicals are methyl radicals.

Even more preferably, the polyorganosiloxane A is the polyorganosiloxane of formula (XII):

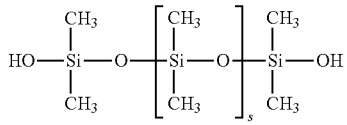

with $1 \leq s \leq 4200$ and preferably 2 s 1500.

The organic groups, identical or different, generally present in the structure of the polyorganosiloxane A are the methyl, ethyl, phenyl or trifluoropropyl radicals. Preferably, at least 80% by number of said organic groups are methyl groups bound directly to the silicon atoms. In the context of the present invention, the α,ω-bis(dimethylhydroxysilyl) polydimethylsiloxanes are more especially preferred.

In the context of the present invention, we may in particular use the α,ω-bis(dimethylhydroxysilyl)polydimethylsiloxanes prepared by the anionic polymerization process described in American patents U.S. Pat. No. 2,891,920 and U.S. Pat. No. 3,294,725.

The polyorganosiloxane A may also be selected from the organosilicic resins bearing at least one hydroxyl or alkoxy group, said groups being either condensable or hydrolyzable, or condensable, and comprising at least two different siloxyl units selected from those of formula M, D, T and Q with:

the siloxyl unit $M=(R^0)_3SiO_{1/2}$,
the siloxyl unit $D=(R^0)_2SiO_{2/2}$,
the siloxyl unit $T=R^0SiO_{3/2}$, and
the siloxyl unit $Q=SiO_{4/2}$;

formulas in which $R^0$ represents a monovalent hydrocarbon-containing group having from 1 to 40 carbon atoms, and preferably from 1 to 20 carbon atoms, or a group —ORe''' with R'''=H or an alkyl radical having from 1 to 40 carbon atoms, and preferably from 1 to 20 carbon atoms;

with the condition that the resins comprise at least one unit T or Q.

Said resin preferably has a content by weight of hydroxy or alkoxy substituents between 0.1 and 10 wt % relative to the weight of the resin, and preferably a content by weight of hydroxy or alkoxy substituents between 0.2 and 5 wt % relative to the weight of the resin.

The organosilicic resins generally have from about 0.001 to 1.5 OH and/or alkoxy group per silicon atom. These organosilicic resins are generally prepared by co-hydrolysis and co-condensation of chlorosilanes such as those of formulas $(R^{19})_3SiCl$, $(R^{19})_2Si(Cl)_2$, $R^{19}Si(Cl)_3$ or $Si(Cl)_4$, the radicals $R^{19}$ being identical or different and generally selected from the linear or branched $C_1$-$C_6$ alkyl, phenyl and trifluoro-3,3,3-propyl radicals. We may mention, as examples of radicals $R^{19}$ of the alkyl type, notably a methyl, an ethyl, an isopropyl, a tert-butyl and an n-hexyl.

As examples of resins, we may mention the silicic resins of the type T(OH), $DT^{(OH)}$, $DQ^{(OH)}$, $DT^{(OH)}$, $MQ^{(OH)}$, $MDT^{(OH)}$, $MDQ^{(OH)}$ or mixtures thereof.

The composition according to the invention may additionally contain a crosslinking agent B. The crosslinking agent is preferably an organosilicon compound bearing more than two hydrolyzable groups per molecule bound to the silicon atoms. Crosslinking agents of this kind are familiar to a person skilled in the art and are commercially available.

The crosslinking agent B is preferably a silicon compound in which each molecule comprises at least three hydrolyzable and condensable groups Y, said crosslinking agent B having the following formula (XIII):

$$R^{20}_{(4-j)}SiY_j \quad (XIII)$$

in which:
the symbol $R^{20}$ is a monovalent hydrocarbon radical comprising from 1 to 30 carbon atoms,
the symbols Y, which may be identical or different, are selected from the group consisting of the alkoxy, alkoxy-alkylene-oxy, amino, amido, acylamino, aminoxy, iminoxy, ketiminoxy, acyloxy or enoxy groups, and preferably Y is an alkoxy, acyloxy, enoxy, ketiminoxy or oxime group,
the symbol j=2, 3 or 4, and preferably j=3 or 4.

Examples of groups Y are the same as those mentioned above when the symbol Z is a hydrolyzable and condensable group, i.e. different from a hydroxyl group.

The crosslinking agents B are products available on the silicones market. Moreover, their use in the room-temperature-vulcanizable compositions is known. It is mentioned notably in French patents FR 1 126 411, FR 1 179 969, FR 1 189 216, FR 1 198 749, FR 1 248 826, FR 1 314 649, FR 1 423 477, FR 1 432 799 and FR 2 067 636.

The crosslinking agent B has at least one hydrolyzable group such as:
acyloxy of formula —O—CO—R'''',
alkoxy of formula —O—R'''',
amino of formula —NR$^{21}$R$^{22}$,
amido of formula —NR$^{21}$COR$^{22}$,
alkenyloxy of formula —O—CR$^{21}$═CHR$^{22}$,
aminoxy of formula —O—NR$^{21}$R$^{22}$,
ketiminoxy of formula —O—N═CR$^{21}$R$^{22}$ or

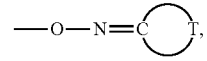

where R'''' represents an alkyl or aryl radical having from 1 to 15 carbon atoms, $R^{21}$ and $R^{22}$, which may be identical or different, represent alkyl or aryl radicals containing from 1 to 8 carbon atoms and T represents an alkylene radical containing from 4 to 8 carbon atoms. Among the radicals R'''', $R^{21}$ and $R^{22}$, we may mention quite particularly the methyl, ethyl, cyclohexyl and phenyl radicals. Among the radicals T, we may mention quite particularly those of formula: —(CH$_2$)$_4$—, —(CH$_2$)$_5$— and —(CH$_2$)$_6$—.

As other examples of crosslinking agent B, we may mention the alkoxysilanes and the products of partial hydrolysis of this silane of the following general formula (XIV):

$$R^{23}_kSi(OR^{24})_{(4-k)} \quad (XIV)$$

in which:
the symbols $R^{23}$, which may be identical or different, represent alkyl radicals having from 1 to 8 carbon atoms, such as the methyl, ethyl, propyl, butyl, pentyl, ethyl-2-hexyl, octyl and decyl radicals, $C_3$-$C_6$ oxyalkylene radicals,
the symbol $R^{24}$ represents an aliphatic hydrocarbon group, saturated or unsaturated, linear or branched, a carbocyclic group, saturated or unsaturated and/or aromatic, monocyclic or polycyclic, and
k is equal to 0, 1 or 2.

As examples of $C_3$-$C_6$ oxyalkylene radicals, we may mention the following radicals:
CH$_3$OCH$_2$CH$_2$—
CH$_3$OCH$_2$CH(CH$_3$)—

CH₃OCH(CH₃)CH₂—
C₂H₅OCH₂CH₂CH₂—

The acyloxysilane crosslinking agents have long been well known. They are described notably in patents U.S. Pat. No. 3,077,465, U.S. Pat. No. 3,382,205, U.S. Pat. No. 3,701,753, U.S. Pat. No. 3,957,714, U.S. Pat. No. 4,115,356, U.S. Pat. No. 4,273,698, FR 2 429 811 and FR 2 459 820.

As examples of alkoxysilanes, we may mention those of formula:

Si(OCH₃)₄
Si(OCH₂CH₃)₄
Si(OCH₂CH₂CH₃)₄
(CH₃O)₃SiCH₃
(C₂H₅O)₃SiCH₃
(CH₃O)₃Si(CH=CH₂)
(C₂H₅O)₃Si(CH=CH₂)
(CH₃O)₃Si(CH₂—CH=CH₂)
(CH₃O)₃Si[CH₂—(CH₃)C=CH₂]
(C₂H₅O)₃Si(OCH₃)
Si(OCH₂—CH₂—OCH₃)₄
CH₃Si(OCH₂—CH₂—OCH₃)₃
(CH₂=CH)Si(OCH₂CH₂OCH₃)₃
C₆H₅Si(OCH₃)₃
C₆H₅Si(OCH₂—CH₂—OCH₃)₃.

The ketiminoxysilane crosslinking agents have long been well known. They are described for example in French patents FR 1 314 649, FR 1 371 250, American patents U.S. Pat. No. 3,678,003 and U.S. Pat. No. 3,986,999, in British patent GB 1 468 467, in Belgian patent BE 901 479 and in European patent EP 157 580.

As examples of ketiminoxysilanes, we may mention those of formula:

CH₃Si[—O—N=C(CH₃)₂]₃
CH₃Si[—O—N=C(CH₃)C₂H₅]₃
CH₂=CHSi[—O—N=C(CH₃)C₂H₅]₃
C₆H₅Si[—O—N=C(CH₃)₂]₃
CH₃Si[—O—N=C(C₂H₅)(CH₂)₃CH₃]₃
[(CH₃)₂C=N—O—]Si[—O—N=C(CH₃)C₂H₅]₃
CH₃Si[—O—N=C(CH₃CH(C₂H₅)(CH₂)₃CH₃]₃
CH₃Si[—O—N=C(CH₃CH(C₂H₅)(CH₂)₃CH₃]₃

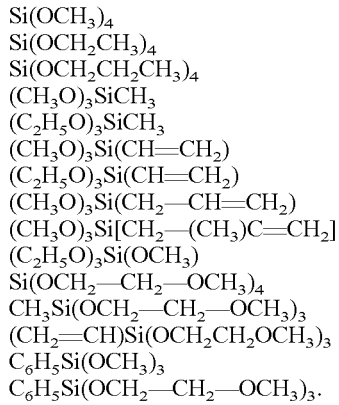

As examples of acyloxysilanes, we may mention those of formula:

CH₃Si(OCOCH₃)₃
C₂H₅Si(OCOCH₃)₃
CH₂=CHSi(OCOCH₃)₃
C₆H₅Si(OCOCH₃)₃
CH₃Si[OCOCH(C₂H₅)—(CH₂)₃—CH₃]
CF₃CH₂CH₂Si(OCOC₆H₅)₃
CH₃Si(OCOCH₃)₂[OCOH(C₂H₅)—(CH₂)₃—CH₃]
CH₃COOSi[OCOCH(C₂H₅)—(CH₂)₃—CH₃]

As other examples of crosslinking agent B, we may mention ethyl polysilicate, or n-propyl polysilicate.

Among the crosslinking agents B, those more particularly preferred are the alkoxysilanes, ketiminoxysilanes, alkyl silicates and alkyl polysilicates, in which the organic radicals are alkyl radicals having from 1 to 4 carbon atoms.

The following crosslinking agents B are preferred, which may be used alone or mixed:

ethyl polysilicate and n-propyl polysilicate;

alkoxysilanes such as dialkoxysilanes, for example diallcyldialkoxysilanes, trialkoxysilanes, for example alkyltrialkoxysilanes, and tetraalkoxysilanes, and preferably propyltrimethoxysilane, methyltrimethoxysilane, methyltriethoxysilane, ethyltrimethoxysilane, ethyltriethoxysilane, isobutyltrimethoxysilane, isobutyltriethoxysilane, propyltriethoxysilane, tetramethoxysilane, tetraethoxysilane, tetrapropoxysilane, tetrabutoxysilane, 1,2-bis(trimethoxysilyl)ethane, 1,2-bis(triethoxysilyl)ethane, tetra-isopropoxysilane, phenyltriethoxysilane, phenyltrimethoxysilane, vinyltriethoxysilane, vinyltrimethoxysilane and those of the following formulas: CH₂=CHSi(OCH₂CH₂OCH₃)₃, [CH₃][OCH(CH₃)CH₂OCH₃]Si[OCH₃]₂, Si(OC₂H₄OCH₃)₄ and CH₃Si(OC₂H₄OCH₃)₃, acyloxysilanes such as the following acetoxysilanes: tetraacetoxysilane, methyltriacetoxysilane, ethyltriacetoxysilane, vinyltriacetoxysilane, propyltriacetoxysilane, butyltriacetoxysilane, phenyltriacetoxysilane, octyltriacetoxysilane, dimethyldiacetoxysilane, phenylmethyldiacetoxysilane, vinylmethyldiacetoxysilane, diphenyldiacetoxysilane and tetraacetoxysilane, silanes comprising alkoxy and acetoxy groups such as: methylcliacetoxymethoxysilane, methylacetoxydimethoxysilane, vinyldiacetoxymethoxysilane, vinylacetoxydimethoxysilane, methyldiacetoxyethoxysilane and methylacetoxydiethoxysilane, methyltris(methylethyl-ketoximo)silane, 3-cyanopropyltrimethoxysilane, 3-cyanopropyl-triethoxysilane, 3-(glycidyloxy)propyltriethoxysilane, vinyltris(methylethylketoximo)silane, tetra-kis(methylethylketoximo)silane.

Generally from 0.1 to 60 parts by weight of crosslinking agent B are used per 100 parts by weight of polyorganosiloxane A. Preferably, from 0.5 to 15 parts by weight are used per 100 parts by weight of polyorganosiloxane A.

The composition according to the invention may further comprise at least one filler D. The fillers optionally envisaged are preferably mineral fillers. They may notably be siliceous. With regard to siliceous materials, they may perform the role of reinforcing or semi-reinforcing filler. The siliceous reinforcing fillers are selected from colloidal silicas, powders of fumed silica and precipitated silica or mixtures thereof. These powders have an average particle size generally less than 0.1 μm (micrometers) and a BET specific surface area above 30 m²/g, preferably between 30 and 350 m²/g. The semi-reinforcing siliceous fillers such as diatomaceous earths or ground quartz may also be used. Regarding the nonsiliceous mineral materials, they may be used as semi-reinforcing mineral filler or simply as filler. Examples of these nonsiliceous fillers, which may be used alone or mixed, are carbon black, titanium dioxide, aluminum oxide, hydrated alumina, expanded vermiculite, unexpanded vermiculite, calcium carbonate, zinc oxide, mica, talc, iron oxide, barium sulfate and slaked lime. These fillers generally have a granulometry between 0.001 and 300 μm (micrometers) and a BET surface area less than 100 m²/g. The fillers used may conveniently be a mixture of quartz and silica, but the invention is not limited to this. The fillers may be treated with any suitable product. In weight terms, it is preferable to use an amount of filler between 1 and 50 wt %, preferably between 1 and 40 wt % relative to the total constituents of the composition.

In the case of calcium carbonate, this filler may be a synthetic calcium carbonate obtained chemically, better known by the term "precipitated calcium carbonate", or a ground natural calcium carbonate prepared for example from chalk, calcite, marble or from a mixture thereof. These two classes of calcium carbonate may have undergone an unreactive surface treatment. This type of treatment consists of covering the surface of the fillers with an organic substance. Among organic compounds of this kind that may be used, the fatty acids and mainly stearic acid or a salt thereof are preferred. A useful calcium carbonate may also result from a reactive surface treatment carried out with coupling agents such as organotrialkoxysilanes, which are widely used as coupling agents.

Preferably, the ground natural calcium carbonate has a specific surface strictly below 3 m²/g, measured by the BET method, and has been surface-treated with at least one fatty acid containing from 10 to 24 carbon atoms or a respective salt thereof selected from the calcium, magnesium, or zinc salts or a mixture thereof and preferably has been surface-treated with a stearic acid or a respective calcium, magnesium or zinc salt thereof. Preferably, the amount of ground natural calcium carbonate added to the composition is between 1 and 100 parts by weight relative to the total weight of the composition according to the invention.

In combination with these fillers, it is possible to use mineral and/or organic pigments as well as agents for improving the heat resistance (salts and oxides of rare earths such as cerium oxides and hydroxides) and/or the flame resistance of the elastomers. For example, the cocktails of oxides described in international application WO 98/29488 may be used. Among the agents for improving flame resistance, we may mention halogenated organic derivatives, organic derivatives of phosphorus, platinum derivatives such as chloroplatinic acid (its reaction products with alkanols, ether-oxides), the platinous chloride-olefin complexes. These pigments and agents together represent at most 20% of the weight of the fillers.

The composition according to the invention may also comprise at least one adhesion promoter E such as for example the organosilicon compounds bearing simultaneously:
one or more hydrolyzable groups bound to the silicon atom, and one or more organic groups substituted with radicals comprising a nitrogen atom or selected from the group of the (meth)acrylate, epoxy, and alkenyl radicals, and even more preferably from the group consisting of the following compounds taken alone or mixed:

vinyltrimethoxysilane (VTMO), 3-glycidoxypropyl-trimethoxysilane (GLYMO), methacryloxypropyltrimethoxysilane (MEMO),

[H$_2$N(CH$_2$)$_3$]Si(OCH$_2$CH$_2$)$_3$,

[H$_2$N(CH$_2$)$_3$]Si(OCH$_3$)$_3$

[H$_2$N(CH$_2$)$_3$]Si(OC$_2$H$_5$)$_3$

[H$_2$N(CH$_2$)$_4$]Si(OCH$_3$)$_3$

[H$_2$NCH$_2$CH(CH$_3$)CH$_2$CH$_2$]SiCH$_3$(OCH$_3$)$_2$

[H$_2$NCH$_2$]Si(OCH$_3$)$_3$

[n-C$_4$H$_9$—HN—CH$_2$]Si(OCH$_3$)$_3$

[H$_2$N(CH$_2$)$_2$NH(CH$_2$)$_3$]Si(OCH$_3$)$_3$

[H$_2$N(CH$_2$)$_2$NH(CH$_2$)$_3$]Si(OCH$_2$CH$_2$OCH$_3$)$_3$

-continued

[CH$_3$NH(CH$_2$)$_2$NH(CH$_2$)$_3$]Si(OCH$_3$)$_3$

[H(NHCH$_2$CH$_2$)$_2$NH(CH$_2$)$_3$]Si(OCH$_3$)$_3$

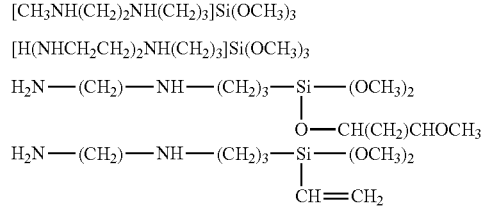

The adhesion promoter E may be present in the silicone composition according to the invention in an amount between 0 and 20 wt %, preferably between 1 and 20 wt %, relative to the weight of the polyorganosiloxane A.

Besides the main constituents, unreactive linear polyorganosiloxane polymers F may be introduced with the intention of acting on the physical characteristics of the compositions according to the invention and/or on the mechanical properties of the elastomers resulting from curing of these compositions.

These unreactive linear polyorganosiloxane polymers F are well known; more particularly they comprise: α,ω-bis(triorganosiloxy)diorganopolysiloxane polymers with from at most 1% of monoorganosiloxy and/or siloxy units, the organic radicals bound to the silicon atoms being selected from the methyl, vinyl and phenyl radicals. Preferably, at least 60% of these organic radicals are methyl radicals and at most 10% are vinyl radicals. The viscosity of these polymers may be between 10 mPa·s and 10$^6$ mPa·s at 25° C.; they are then more or less viscous silicone oils. When the viscosity is above 10$^6$ mPa·s, they are described as silicone gums. Those whose consistency is between 200 and 2000 may preferably be selected. They therefore comprise oils of fluid to viscous appearance and soft to hard gums. They are prepared by the usual techniques described more precisely in French patents FR 978 058, FR 1 025 150, FR 1 108 764, FR 1 370 884. It is preferable to use α,ω-bis(trimethylsiloxy)dimethylpolysiloxane oils of viscosity in the range from 10 mPa·s to 1000 mPa·s at 25° C. These polymers, which perform the role of plasticizers, may be introduced at a rate of at most 70 parts by weight, preferably from 5 to 20 parts by weight per 100 parts by weight of the polyorganosiloxane A.

Other usual auxiliaries and additives may be incorporated in the composition according to the invention. The latter are selected as a function of the applications in which said compositions are used.

The composition according to the invention may comprise the following amounts:
per 100 parts by weight of at least one polyorganosiloxane A as described above,
from 0.1 to 60 parts by weight, preferably from 1 to 15 parts by weight of at least one crosslinking agent B,
a catalytically effective amount of at least one compound C according to the invention, as described above,
from 0 to 150 parts by weight of at least one filler D, and preferably from 0.1 to 150 parts by weight,
from 0 to 20 parts by weight of at least one adhesion promoter E, and preferably from 0.1 to 20 parts by weight, and
from 0 to 150 parts by weight of at least one unreactive linear polyorganosiloxane polymer F, and preferably from 1 to 150 parts by weight.

The compositions of the invention may further comprise usual functional additives. As families of usual functional additives, we may mention:

adhesion modulators,
additives for increasing consistency,
pigments,
additives for heat resistance, for resistance to oils or for fire resistance, for example metal oxides.

More generally, in quantitative terms, the compositions according to the invention may have standard proportions in the field of technology in question, knowing that it is also necessary to take into account the intended application.

According to another embodiment, the composition according to the invention does not contain a catalyst having at least one tin atom in its structure.

According to another variant of the invention, compound C is the only polycondensation catalyst present in said composition, which may optionally contain at least one functionalization catalyst.

According to another embodiment, the invention relates to a single-component composition RTV-1 that is in a single airtight package P and comprises:
a) at least one polyorganosiloxane A as defined above,
b) at least one crosslinking agent B as defined above,
c) a catalytically effective amount of at least one compound C as defined above, and
d) optionally at least one filler D.

The single-component composition RTV-1 is supplied as a single part. It is stable in storage in the absence of water and is cured in the presence of water to form an elastomer. It may be manufactured by mixing the various constituents away from moisture, with or without heating. The catalyst is preferably incorporated at the end. Preferably, mixing is carried out under reduced pressure to promote the escape of volatile materials.

Stored in this way in a confined environment and protected from water and atmospheric moisture, the single-component composition RTV-1 is stable in storage for several months.

The single-component compositions RTV-1, according to the invention, are used as such, i.e. not diluted, or in the form of dispersions in diluents, and are stable in storage in the absence of moisture or water and are cured even at low temperatures (after removal of the solvents in the case of dispersions) in the presence of water, to form elastomers. Single-component compositions RTV-1 are described in detail for example in patents EP 141 685, EP 147 323, EP 102 268, EP 21 859, FR 2 121 289 and FR 2 121 631.

After deposition of the compositions according to the invention, prepared from a single-component composition RTV-1, on solid substrates in moist atmosphere, it is found that a process of curing to elastomer sets in. It takes place from the exterior to the interior of the deposited mass. A skin forms first on the surface, then crosslinking continues into the depth and results in hardening of the silicone elastomer. Complete formation of the skin, which is reflected in a nonsticky feel of the surface, takes several minutes, this period depending on the level of relative humidity of the atmosphere surrounding the compositions and on the ease of crosslinking of the latter. The layer deposited may be of variable thickness, generally between 0.15 mm and several centimeters, preferably between 1 mm and 1 cm.

Moreover, deep curing of the deposited layers, which must be sufficient to allow mold release and handling of the elastomers formed, takes longer. In fact, the length of time depends not only on the aforementioned factors for development of the nonsticky feel, but also on the thickness of the layers deposited, said thickness generally being between 0.5 mm and several centimeters. The single-component compositions may be used for many applications, such as pointing in the building industry, assembly of a great variety of materials (metals, plastics, natural and synthetic rubbers, wood, cardboard, glazed earthenware, brick, ceramic, glass, stone, concrete, masonry units), insulation of electrical conductors, encapsulation of electronic circuits, preparation of molds for making objects in resins or synthetic foams.

The invention further relates to a two-component composition RTV-2, precursor of the composition according to the invention, as defined above, being in two separate packages P1 and P2, characterized in that:
a) package P1 is airtight and comprises:
a catalytically effective amount of at least one compound C according to the invention, as defined above, and
at least one crosslinking agent B as defined above, and
b) package P2 contains neither said compound C nor said crosslinking agent B and comprises:
per 100 parts by weight of at least one polyorganosiloxane A as defined above, and
from 0 to 10 part(s) by weight of water.

A two-component composition RTV-2 is supplied in two separate packages: P1, which contains the catalyst and is airtight, and P2. They are packaged after incorporation of the catalyst in two separate fractions, where one of the fractions may for example only contain the catalyst according to the invention or a mixture with the crosslinking agent. The two-component compositions RTV-2 according to the invention are also produced by mixing the various constituents in suitable apparatus. Two-component compositions RTV-2 are described in detail for example in patents EP 118 325, EP 117 772, EP 10 478, EP 50 358, EP 184 966, U.S. Pat. No. 3,801,572 and U.S. Pat. No. 3,888,815, cited as reference.

The two-component composition RTV-2 makes it possible to obtain the composition according to the invention, after mixing the two parts P1 and P2. It is a "precursor" composition of the composition according to the invention. Each part of the two-component composition RTV-2 may be produced by mixing the various constituents. The two parts may be stored and marketed in the form of a kit. At the time of use, the two parts are mixed, and this mixture can be deposited on a solid substrate. The layer deposited may be of variable thickness, generally between 0.15 mm and several centimeters, preferably between 1 mm and 1 cm. Bringing the polyorganosiloxane A, water and compound C, which performs the role of catalyst, into contact triggers the reactions leading to curing of the composition, until a completely hard elastomer is obtained.

The composition according to the invention advantageously has curing kinetics comparable to those of the compositions currently available on the market containing a tin-based catalyst, both in terms of the rate of skin formation and the rate of deep curing. Moreover, advantageously, the performance of this composition is not altered by the presence of adhesion promoter.

The compositions according to the invention are particularly useful for applications of molding, especially when they are in the two-component form RTV-2. For use of the compositions according to the invention in this application, the techniques of casting or of application by spatula, by brush or by spraying may be used.

As examples of molding techniques, we may mention:
"block molding", which is intended for the production of self-supporting molds, in one or more parts, by simple casting of the composition after mixing the two parts of the RTV-2 in the liquid state on the initial pattern. This method is preferred for relatively simple shapes without large undercuts;

"molding under cover in one or two parts", and

"molding by stamping", which is preferred for making the cavity of inclined, vertical or overhanging patterns, generally of large dimensions or when it is impossible to move the pattern.

The invention further relates to a silicone elastomer obtained:

after leaving the composition according to the invention, as described above, to cure in the presence of water or atmospheric moisture; or after bringing the contents of package P of the single-component composition RTV-1 according to the invention, as described above, into contact with atmospheric moisture, and leaving said contents to harden; or after mixing the contents of packages P1 and P2 of the two-component composition RTV-2 according to the invention, as described above, and leaving the mixture to harden.

The silicone elastomer obtained advantageously has hardness at least equivalent to that of the elastomers obtained from compositions containing a tin-based catalyst. They may moreover be translucent and not undergo yellowing over time.

The invention further relates to a method of coating the composition according to the invention, as defined above, on a flexible substrate S comprising the following steps a), b) and c):

a) preparing a composition according to the invention, as defined above, b) then depositing said composition on said flexible substrate S, continuously or discontinuously, and c) leaving said silicone composition according to the invention to harden in the presence of moisture supplied by the ambient air or by adding water beforehand, so as to form a silicone elastomer.

According to a variant of the method according to the invention, the composition is prepared in step a) after mixing the contents of packages P1 and P2 of the two-component composition RTV-2 according to the invention, as defined above, or starting from the contents of package P of the single-component composition RTV-1 according to the invention, as defined above.

Coating of silicone compositions according to the invention on flexible substrates is intended for numerous applications. For example, when the flexible substrate is a textile, the aim is to provide waterproofing properties, or when the substrate is paper or a polymer such as PVC, PET etc., anti-adhesion properties are most often required.

Thus, once applied on a substrate, the silicone composition according to the invention hardens owing to atmospheric moisture and/or through the presence of water in the composition, to form a solid coating of silicone elastomer. In these liquid silicone coating compositions, the silicone phase may be diluted in a solvent.

The flexible substrates S coated with an antiadhesion silicone film or silicone layer cured by crosslinking are preferably selected from the group consisting of substrates of textile, paper, polyvinyl chloride, polyester, polypropylene, polyamide, polyethylene, polyurethane or polyethylene terephthalate.

In the sense of the invention, textile is a general term that includes all textile structures. The textiles may consist of threads, fibers, filaments and/or other materials. They notably comprise flexible fabrics, whether they are woven, glued, knitted, plaited, made of felt, needle-punched, stitched, or produced by some other method of manufacture.

These textiles may be openwork, i.e. may comprise empty spaces not consisting of textile. For coating of the silicone composition of the invention to be effective, it is preferable for the smallest of the dimensions of these empty spaces to be less than 5 mm, notably less than 1 mm.

According to the invention, any type of flexible substrate S made of textile may be used. As a guide, we may mention:

natural textiles, such as textiles of vegetable origin, such as cotton, flax, hemp, jute, coconut, the cellulose fibers of paper; and textiles of animal origin, such as wool, hair, leather and silks;

artificial textiles, such as cellulose textiles, such as cellulose or derivatives thereof; and proteinaceous textiles of animal or vegetable origin; and synthetic textiles, such as polyester, polyamide, polymallic alcohols, polyvinyl chloride, polyacrylonitrile, poly olefins, acrylonitrile, (meth)acrylate-butadiene-styrene copolymers and polyurethane.

The synthetic textiles obtained by polymerization or polycondensation may notably comprise various types of additives in their matrixes, such as pigments, delustring agents, matting agents, catalysts, thermal stabilizers and/or light stabilizers, antistatic agents, fireproofing agents, antibacterial, antifungal, and/or antiacarid agents.

As types of flexible textile substrates, we may notably mention substrates obtained by rectilinear intertwining of threads or fabrics, substrates obtained by curvilinear interlacing of threads or knitted fabrics, mixture fabrics or tulles, nonwoven substrates and composite substrates. Among the numerous kinds of textile substrates that may be used in the method of the invention, we may mention: felts, denims, woven jacquards, needle-bonded fabrics, stitched fabrics, crocheted fabrics, grenadines, laces and serrated, damasks, voiles, alpacas, baratheas, dimities, bouclé fabrics, brocades, calicoes, velours, canvas, chiffons, flocks, bonded fabrics, bunting, braided fabrics, faille, foulards, gauzes, geotextiles, jaspers, matelassé, tufted fabrics, organzas, pleated fabrics, ribbons and toiles.

The flexible textile substrate S used in the method of the present invention may consist of one or more textiles, which may be identical or different, assembled in various ways. The textile may be mono- or multilayer. The textile substrate may for example consist of a multilayer structure that may be produced by various assembly means, such as mechanical means such as sewing, welding, or spot or continuous gluing.

The flexible textile substrate S may, in addition to the coating process according to the present invention, undergo one or more other treatments, also called finishing treatment. These other treatments may be carried out before, after and/or during said coating process of the invention. As other treatments, we may notably mention: dyeing, printing, laminating, coating, assembly with other materials or textile surfaces, washing, defatting, preforming or fixing.

According to a preferred embodiment of the invention, the flexible textile substrate S is a lace or an elastic bandage.

The textiles thus obtained, as such or converted into textile articles, can be used in many applications, such as, for example, in the area of clothing, notably lingerie such as lace of stocking tops or brassieres, and hygiene articles, such as compression bandages or dressings. These textile articles may be repositioned at different points of the body or of clothing for example owing to the adhesion supplied by the silicone elastomer.

In practice, the rate of deposition of the composition according to the invention on the flexible substrate S is between 0.1 g/m$^2$ and 1 g/m$^2$, preferably between 0.3 g/m$^2$ and 0.5 g/m$^2$, which corresponds to thicknesses of the order of a micrometer.

Other aims, features and advantages of the invention will become clear from the following examples, which are given purely for illustration and are not in any way limiting.

EXAMPLES

Notation

OsBu: sec-butanolate
OnBu: n-butanolate
OtBu: tert-butanolate
OBO: 2-butyloctanolate
OC$_4$H$_9$: butanolate (mixture of linear and branched compounds)
OEH: 2-ethylhexanolate
OEt: ethanolate
OiPr: isopropanolate
OnPr: n-propanolate
OPr2Me: 2-methylpropan-1-olate
EAA: ethyl acetoacetate
EEA: ethyl ethyl acetate
EPA: propionyl ethyl acetate
E2EA: 2-ethyl ethyl acetoacetate
F.EEA: trifluoro-ethyl acetoacetate
t.EAA: t-butyl ethyl acetoacetate
C4EA: cyclopropyl ethyl acetoacetate
PrOH: propanol
PAA: propyl acetoacetonate
EPAA: propionyl ethyl acetoacetate
acac: acetylacetone
F.acac.F: hexafluoroacetylacetone
Ph.acac.F: 4,4,4-trifluoro-1-phenyl-1,3-butanedione
Ph.acac.Ph: 1,3-diphenyl-1,3-propanedione
t.acac: 2,2,6,6-tetramethyl-3,5-heptanedione
diPrm: diisopropyl malonate
Aamid: acetoacetamide
NacNac: bis-N,N'-(2-phenylethyl)-2,4-diiminopentane
MA: methyl acrylate
DBU: 1,8-diazabicyclo(5.4.0)undec-7-ene

Example 1: Synthesis and Analysis of the Heterometallic Alkoxide Complex AlTi(OsBu)$_3$(OnBu)$_4$ The monometallic alkoxides Al(OsBu)$_3$ and Ti(OnBu)$_4$ were ordered from Sigma-Aldrich and were used on receipt.

Al(OsBu)$_3$ and Ti(OnBu)$_4$ were mixed in the molar proportions of 1 mole per 1 mole and were stirred for 2 hours at room temperature. The oil obtained quantitatively was then characterized by infrared.

In the spectrum of the heterometallic complex, the appearance of two new, very intense bands was found at 1035.8 cm$^{-1}$ and 996.2 cm$^{-1}$, which correspond to the vibrations of the C—O bonds in the Al—C—O—C—Ti chain. The bands at 611.7 cm$^{-1}$ and at 515.2 cm$^{-1}$, also very intense, correspond to the vibrations of the metal-O bonds in the Al—O—Ti chain. The other bands of medium or low intensity correspond to the bands visible in the starting products, but with different resonance frequencies. These changes clearly show a novel chemical environment around the metals Al and Ti, and therefore the creation of a novel chemical species.

Example 2: Synthesis of Heterometallic Alkoxide Complexes

A series of heterometallic alkoxide complexes was prepared by the following method:

The monometallic alkoxides of aluminum Al(OnBu)$_3$, Al(OsBu)$_3$, Al(OBO)$_3$, Al(OiPr)$_3$, Al(OEH)$_3$, of magnesium Mg(OEt)$_2$, Mg(OBO)$_2$, of zirconium Zr(OnBu)$_4$, Zr(OBO)$_4$, Zr(OnBu)$_4$, Zr(OnPr)$_4$, Zr(OEH)$_4$, Zr(OEt)$_4$ and of titanium Ti(OBO)$_4$, Ti(OnBu)$_4$, Ti(OiPr)$_4$ and Ti(OEH)$_4$, were obtained from Sigma-Aldrich and were used on receipt or concentrated under reduced pressure.

The monometallic alkoxide species selected as a function of the desired complex were mixed in the desired molar proportions and were stirred for 2 hours at room temperature. An oil was obtained quantitatively.

The heterometallic complexes synthesized are listed below. The general formulas shown represent the composition of the complex and the molar ratios between the various atoms or groups of atoms as they ought to be according to the composition of the reaction mixture and assuming that the reactions go to completion. A person skilled in the art will of course understand that the reaction products obtained may differ from these general formulas.

Aluminum-zirconium complexes:
AlZr(OnBu)$_7$
AlZr(OBO)$_7$
AlZr(OsBu)$_3$(OnBu)$_4$
Al$_{0.1}$Zr(OsBu)$_{0.3}$(OnBu)$_4$
Al$_{0.2}$Zr(OsBu)$_{0.6}$(OnBu)$_4$
Al$_{0.3}$Zr(OsBu)$_{0.9}$(OnBu)$_4$
Al$_{0.4}$Zr(OsBu)$_{1.2}$(OnBu)$_4$
Al$_{0.5}$Zr(OsBu)$_{1.5}$(OnBu)$_4$
Al$_{0.6}$Zr(OsBu)$_{1.8}$(OnBu)$_4$
Al$_{0.7}$Zr(OsBu)$_{2.1}$(OnBu)$_4$
Al$_{0.8}$Zr(OsBu)$_{2.4}$(OnBu)$_4$
Al$_{0.9}$Zr(OsBu)$_{2.7}$(OnBu)$_4$
Al$_{1.1}$Zr(OsBu)$_{3.3}$(OnBu)$_4$
Al$_{1.2}$Zr(OsBu)$_{3.6}$(OnBu)$_4$
Al$_{1.3}$Zr(OsBu)$_{3.9}$(OnBu)$_4$
Al$_{1.4}$Zr(OsBu)$_{4.2}$(OnBu)$_4$
Al$_{1.5}$Zr(OsBu)$_{4.5}$(OnBu)$_4$
Al$_{1.6}$Zr(OsBu)$_{4.8}$(OnBu)$_4$
Al$_{1.7}$Zr(OsBu)$_{5.1}$(OnBu)$_4$
Al$_{1.8}$Zr(OsBu)$_{5.4}$(OnBu)$_4$
Al$_{1.9}$Zr(OsBu)$_{5.7}$(OnBu)$_4$
AlZr$_{0.1}$(OsBu)$_3$(OnBu)$_{0.4}$
AlZr$_{0.2}$(OsBu)$_3$(OnBu)$_{0.8}$
AlZr$_{0.3}$(OsBu)$_3$(OnBu)$_{1.2}$
AlZr$_{0.4}$(OsBu)$_3$(OnBu)$_{1.6}$
AlZr$_{0.5}$(OsBu)$_3$(OnBu)$_2$
AlZr$_{0.6}$(OsBu)$_3$(OnBu)$_{2.4}$
AlZr$_{0.7}$(OsBu)$_3$(OnBu)$_{2.8}$
AlZr$_{0.8}$(OsBu)$_3$(OnBu)$_{3.2}$
AlZr$_{0.9}$(OsBu)$_3$(OnBu)$_{3.6}$
Al$_2$Zr(OnPr)$_4$(OiPr)$_6$
Al$_2$Zr(OnBu)$_{10}$
Al$_2$Zr(OnBu)$_4$(OsBu)$_6$
Al$_2$Zr(OEH)$_{10}$
AlZr$_2$(OnBu)$_{11}$
Magnesium-zirconium complexes:
MgZr(OEt)$_6$
MgZr(OBO)$_6$
Mg$_2$Zr(OEt)$_8$
Mg$_3$Zr(OEt)$_{10}$
Mg$_4$Zr(OEt)$_{12}$
MgZr$_2$(OEt)$_{11}$ Aluminum-titanium complexes:
AlTi(OBO)$_7$
AlTi(OsBu)$_3$(OnBu)$_4$
Al$_{0.1}$Ti(OsBu)$_{0.3}$(OnBu)$_4$
Al$_{0.2}$Ti(OsBu)$_{0.6}$(OnBu)$_4$
Al$_{0.3}$Ti(OsBu)$_{0.9}$(OnBu)$_4$
Al$_{0.4}$Ti(OsBu)$_{1.2}$(OnBu)$_4$
Al$_{0.5}$Ti(OsBu)$_{1.5}$(OnBu)$_4$
Al$_{0.6}$Ti(OsBu)$_{1.8}$(OnBu)$_4$
Al$_{0.7}$Ti(OsBu)$_{2.1}$(OnBu)$_4$
Al$_{0.8}$Ti(OsBu)$_{2.4}$(OnBu)$_4$
Al$_{0.9}$Ti(OsBu)$_{2.7}$(OnBu)$_4$
Al$_{1.1}$Ti(OsBu)$_{3.3}$(OnBu)$_4$
Al$_{1.2}$Ti(OsBu)$_{3.6}$(OnBu)$_4$
Al$_{1.3}$Ti(OsBu)$_{3.9}$(OnBu)$_4$
Al$_{1.4}$Ti(OsBu)$_{4.2}$(OnBu)$_4$
Al$_{1.5}$Ti(OsBu)$_{4.5}$(OnBu)$_4$
Al$_{1.6}$Ti(OsBu)$_{4.8}$(OnBu)$_4$
Al$_{1.7}$Ti(OsBu)$_{5.1}$(OnBu)$_4$
Al$_{1.8}$Ti(OsBu)$_{5.4}$(OnBu)$_4$
Al$_{1.9}$Ti(OsBu)$_{5.7}$(OnBu)$_4$
AlTi$_{0.1}$(OsBu)$_3$(OnBu)$_{0.4}$
AlTi$_{0.2}$(OsBu)$_3$(OnBu)$_{0.8}$
AlTi$_{0.3}$(OsBu)$_3$(OnBu)$_{1.2}$
AlTi$_{0.4}$(OsBu)$_3$(OnBu)$_{1.6}$
AlTi$_{0.5}$(OsBu)$_3$(OnBu)$_{2.0}$
AlTi$_{0.6}$(OsBu)$_3$(OnBu)$_{2.4}$
AlTi$_{0.7}$(OsBu)$_3$(OnBu)$_{2.8}$
AlTi$_{0.8}$(OsBu)$_3$(OnBu)$_{3.2}$
AlTi$_{0.9}$(OsBu)$_3$(OnBu)$_{3.6}$
Al$_2$Ti(OiPr)$_{10}$
Al$_2$Ti(OnBu)$_{10}$
Al$_2$Ti(OEH)$_{10}$ In addition, the following commercial complexes were used:
Aluminum-zirconium complex: Al$_2$Zr(OC$_4$H$_9$)$_{10}$
Magnesium-zirconium complex: MgZr(OC$_4$H$_9$)$_6$
Aluminum-titanium complex: Al$_2$Ti(OC$_4$H$_9$)$_{10}$
Magnesium-titanium complex: MgTi(OC$_4$H$_9$)$_6$ Example 3: Synthesis of Heterometallic Chelated Complexes The monometallic alkoxides Mg(OEt), Al(OiPr)$_3$, Al(OsBu)$_3$, Zr(OnPr)$_4$, Zr(OnBu)$_4$, Zr(OnBu)$_2$(acac)$_2$, Zr(acac)$_4$, Ti(OiPr)$_4$, Ti(OnBu)$_4$ and Ti(EAA)$_2$(OPr2Me)$_2$ were obtained from Sigma-Aldrich and were used on receipt or concentrated under reduced pressure.

Monometallic chelated complexes Mg(EAA)$_2$, Al(OsBu)$_2$ (EAA)$_2$, Al(EAA)$_3$, Zr(OnPr)$_2$(EAA)$_2$, Zr(OnPr)$_2$ (EEA)$_2$, Al(OnPr)$_2$(EEA)$_2$, Al(OnPr)$_2$(EP A)$_2$, Zr(OnPr)$_2$(E2EA)$_2$, Zr(OnPr)$_2$(F.EEA)$_2$, Zr(OnPr)$_2$(t.E AA)$_2$, Zr(OnPr)$_2$(C$_4$EA)$_2$, Zr(OnPr)(EAA)$_3$, Zr(OnPr)(E-PAA)$_3$, Zr(EAA)$_4$.PrOH, Zr(PAA)$_4$.PrOH, Zr(EP AA)$_4$.EPAA, Zr(OnPr)$_2$(acac)$_2$, Zr(OnPr)$_2$(F.acac.F)$_2$, Zr(OnPr)$_2$(Ph.acac.F)$_2$, Zr(OnPr)$_2$(Ph.acac.Ph)$_2$, Zr(OnPr)$_2$ (t.acac)$_2$, Zr(OnPr)$_2$(diPrm)$_2$, Zr(diPrm)$_4$, Zr(OnPr)$_2$ (Aamid)$_2$, Zr(OnPr)$_2$(NacNac)$_2$, Zr(OnPr)$_2$(MA)$_2$, Zr(OnPr)$_2$ (DBU)$_2$.PrOH and Ti(EAA)$_2$(OiPr)$_2$ were prepared by the following method:

1 equivalent of the corresponding monometallic alkoxide complex was diluted in toluene. Then 1, 2, 3 or 4 equivalents of a corresponding ligand were added to the above mixture. The solution was then heated at 140° C. so as to distill the azeotropic mixture formed by the alcohol released and the toluene. The residual solvent was evaporated.

The heterometallic chelated complexes were prepared according to 3 routes of synthesis.

Route 1: Combining a monometallic alkoxide complex with a monometallic chelated complex AlTi(EAA)$_3$(OnBu)$_4$ was prepared by mixing 1 mole of Al(EAA)$_3$ with 1 mole of Ti(OnBu)$_4$. The mixture was stirred for 2 hours at room temperature. When difficulties of solubility persisted, the mixture was heated to 65° C.

The complexes AlZr(EAA)$_3$(OnPr)$_4$, AlZr(EAA)$_7$, AlZr$_{0.5}$(EAA)$_5$, Al$_2$Zr(EAA)$_{10}$, AlZr(OsBu)$_3$(OnPr)$_4$ (diPrm)$_2$, MgZr(EAA)$_6$, MgTi(EAA)$_4$(OiPr)$_2$ were prepared in the same way with the corresponding starting complexes in the corresponding proportions.

Route 2: Ligand exchange

AlZr(EAA)$_7$ was prepared from 4 g of AlZr(OnBu)$_7$ diluted in 15 mL of toluene. 7 equivalents of ethyl acetoacetonate were then added to the above mixture, which was heated to 130° C. Then the azeotropic mixture formed by the butanol released and the toluene was distilled and the residual solvent was evaporated.

Route 3: One-pot synthesis

AlZr(EAA)$_3$(OnPr)$_4$, AlZr(EAA)$_3$(OnBu)$_4$, AlZr(OiPr)$_5$ (PAA)$_2$, AlTi(EAA)$_3$(OnBu)$_4$ and AlTi(PAA)$_2$(OiPr)$_5$ and Al$_2$Zr(EAA)$_6$(OnPr)$_4$ were synthesized in one pot. For this, 2 or 3 equivalents of ethyl acetoacetonate or of propyl acetoacetonate were added to one equivalent of Zr(OnBu)$_4$, of Ti(OnBu)$_4$ or of Al(OiPr)$_3$. The mixture was immediately heated at 70° C. until a homogeneous mixture was obtained, which was concentrated under reduced pressure to release the n-butanol or isopropanol. After this, one equivalent of Al(OiPr)$_3$, of Zr(OnBu)$_4$, of Ti(OnBu)$_4$ or of Zr(OnPr)$_4$ was added directly and, after stirring for 2 hours at room temperature, the desired heterometallic complexes were obtained in the form of light yellow oil.

Example 4: Catalytic Properties of the Heterometallic Complexes

To test the catalytic properties of the metal complexes, pasting compositions were prepared. For this, 3464 g of an α,ω-hydroxy-polydimethylsiloxane oil of viscosity 20 000 mPa·s was mixed with 120 g of vinyltrimethoxysilane (VTMO). 16 g of lithia diluted to 0.4 wt % in methanol was then added to the mixture obtained. After stirring for 5 minutes, 400 g of AE55 pyrogenic silica was added. The mixture was concentrated under reduced pressure and then stored in a closed cartridge protected from moisture.

For each test, 25 g of this paste and an amount of catalyst were mixed in a high-speed mixer (2×20 seconds at 2000 rev/min). The catalytic activity of each composition was then evaluated by taking several measurements in constant conditions of temperature and hygrometry (23° C. at 50%):

The skin formation time (SFT): time at the end of which surface crosslinking is observed. It is effected with a beech rod on a film with a thickness of 2 mm.

Hardness (Shore A): this reflects formation of the three-dimensional network. It was measured on the one hand on the superposition of 3 cords with thickness of 2 mm, and on the other hand on a single cord with thickness of 6 mm, over increasing times (5 h, 1 and 7 days). Two measurements were taken on the cord with thickness of 6 mm: ">" corresponds to the hardness on the upper part of the cord and "<" corresponds to the lower or confined part of the cord. "NC" denotes not crosslinked, "NS" denotes not strippable, "S" denotes strippable and "C" denotes sticky. These letters were used when the hardness was less than 5.

The data not determined are designated "n.d".
The tests were carried out on heterometallic catalysts according to the invention and on catalysts of the prior art:
dibutyltin dilaurate (DBTDL)
tetrabutoxytitanium Ti(OnBu)$_4$
tri(sec-butoxy)aluminum Al(OsBu)$_3$
tetrapropoxy zirconium Zr(OnPr)$_4$ The results for the catalysts of the alkoxide type in equimolar amounts are presented in Table 1:

TABLE 1

| | Catalysts | mmol/ OH | wt % | SFT 2 mm | HSA 5 h 3 × 2 mm | HSA 1 d | HSA 7 d 6 mm <> |
|---|---|---|---|---|---|---|---|
| reference catalysts | DLDBE | 2.1 | 2.7% | 8 min | S | 26 | 33 30 |
| | Ti(OnBu)$_4$ | 2.1 | 1.4% | 15 min | 20 | 29 | 30 25 |
| | Al(OsBu)$_3$ | 2.1 | 1.0% | NC | NC | NC | NC |
| | Zr(OnPr)$_4$ | 2.1 | 1.4% | n.d. | NS | NS | 18 19 |
| Ex. 1 | AlZr(OsBu)$_3$(OBu)$_4$ | 2.1 | 2.6% | n.d. | 26 | 27 | 30 25 |
| Ex. 2 | Al$_{1.4}$Zr(OsBu)$_{4.2}$(OnBu)$_4$ | 2.1 | 2.9% | 5 min | 10 | 23 | 30 25 |
| Ex. 3 | Al$_2$Zr(OC$_4$H$_9$)$_{10}$ | 2.1 | 3.3% | 5 min | 19 | 29 | 29 24 |
| Ex. 4 | AlTi(OsBu)$_3$(OnBu)$_4$ | 2.1 | 2.5% | n.d. | 28 | 33 | 33 28 |
| Ex. 5 | Al$_{0.5}$Ti(OsBu)$_{1.5}$(OnBu)$_4$ | 2.1 | 1.9% | 8 min | 22 | 28 | 32 26 |
| Ex. 6 | Al$_2$Ti(OC$_4$H$_9$)$_{10}$ | 2.1 | 3.2% | 10 min | 25 | 28 | 31 26 |
| Ex. 7 | AlTi$_{0.2}$(OsBu)$_3$(OnBu)$_{0.8}$ | 2.1 | 1.3% | 8 min | 14 | 29 | 30 28 |

The results for the catalysts of the mixed chelate type in equimolar amounts are presented in Table 2:

TABLE 2

| | Catalysts | mmol/ OH | wt % | SFT 2 mm | HSA 5 h 3 × 2 mm | HSA 1 d | HSA 7 d 6 mm <> |
|---|---|---|---|---|---|---|---|
| reference catalysts | DLDBE | 2.1 | 2.7% | 8 min | S | 26 | 33 30 |
| | Ti(OnBu)$_4$ | 2.1 | 1.4% | 15 min | 20 | 29 | 30 25 |
| | Al(OsBu)$_3$ | 2.1 | 1.0% | NC | NC | NC | NC |
| | Zr(OnPr)$_4$ | 2.1 | 1.4% | n.d. | NS | NS | 18 19 |
| Ex. 8 | AlZr(EAA)$_7$ | 2.1 | 4.3% | 6 min | 25 | 31 | 31 29 |
| Ex. 9 | AlZr(OsBu)$_3$(OnPr)$_4$(diPrm)$_2$ | 2.1 | 3.7% | 10 min | 16 | 29 | 30 26 |
| Ex. 10 | AlTi(OiPr)$_5$(PAA)$_2$ | 2.1 | 2.0% | 6 min | 26 | 26 | 32 24 |

The heterometallic complexes lead quickly, in less than 15 minutes, to elastomers as hard as those obtained with reference catalysts such as dibutyltin dilaurate (DBTDL) and tetrabutoxytitanium Ti(OnBu)$_4$.

Example 5: Comparison of Monometallic/Heterometallic Complexes

The catalytic activity of the heterometallic complexes according to the invention was compared with the catalytic activity of the mixtures of the monometallic complexes.

For this, pastes were prepared as described in example 4, and were then mixed on the one hand with a heterometallic complex according to the invention and on the other hand with the corresponding in situ mixture of two monometallic complexes.

The results are presented in Table 3:

TABLE 3

| | Catalysts | mmol/ OH | wt % | SFT 2 mm | HSA 5 h 3 × 2 mm | HSA 1 d | HSA 7 d 6 mm <> |
|---|---|---|---|---|---|---|---|
| Ex. 11 | AlZr(OsBu)$_3$(OnBu)$_4$ | 1.6 | 2.0% | 8 min | 3 | 13 | 26 20 |
| comparative | Al(OsBu)$_3$ | 1.6 | 1.2% | 12 min | 5 | 7 | 20 15 |
| | Zr(OnBu)$_4$ | 1.6 | 0.8% | | | | |

TABLE 3-continued

| | Catalysts | mmol/ OH | wt % | SFT 2 mm | HSA 5 h 3 × 2 mm | HSA 1 d 3 × 2 mm | HSA 7 d 6 mm <> |
|---|---|---|---|---|---|---|---|
| Ex. 12 comparative | AlTi(OsBu)$_3$(OnBu)$_4$ | 1.7 | 2.0% | 10 min | 17 | 27 | 31 25 |
| | Al(OsBu)$_3$ | 1.7 | 1.2% | 7 min | 16 | 27 | 30 22 |
| | Ti(OnBu)$_4$ | 1.7 | 0.8% | | | | |
| Ex. 13 comparative | AlZr(EAA)$_3$(OnPr)$_4$ | 1.3 | 2.0% | 8 min | 14 | 27 | 32 27 |
| | Al(EAA)$_3$ | 1.3 | 1.1% | 24 min | NS | NS | 17 15 |
| | Zr(OnPr)$_4$ | 1.3 | 0.9% | | | | |
| Ex. 14 comparative | AlTi(EAA)$_3$(OnBu)$_4$ | 1.3 | 2.0% | 7 min | 21 | 29 | 34 28 |
| | Al(EAA)$_3$ | 1.3 | 1.1% | 20 min | 5 | 20 | 29 26 |
| | Ti(OnBu)$_4$ | 1.3 | 0.9% | | | | |

The preformed heterometallic catalysts are observed to have better reactivity than the monometallic alkoxides added in situ during the test. It is thought that when the complexes are brought into contact in situ, no association reaction of the complexes is possible, since they are in a greatly diluted medium. The hardness difference can also be explained by the formation of novel species leading to novel reactivity relative to the monometallic species. Thus, it is necessary to preform the heterometallic complex before adding it to the silicone composition.

It is found, moreover, that the compositions containing a zirconium-based catalyst, notably the Al—Zr complexes, remain translucent even after accelerated aging (2-mm films held at 100° C. for 7 days).

It should also be noted that the compositions containing a heterometallic chelated catalyst are more stable after accelerated aging (cartridges held at 50° C. for 3 weeks) than those containing a heterometallic alkoxide catalyst.

Example 6: Behavior in the Presence of an Adhesion Promoter

Pastes were prepared as described in example 4 with in addition 1 wt % of an aminated silane (3-(2-aminoethyl-amino)propyl-dimethoxymethylsilane), used conventionally as an adhesion promoter. These pastes were mixed with a catalyst, and the catalytic activity of each composition was then evaluated as in example 3.

The results of the tests on the alkoxide catalysts in the presence of adhesion promoter are presented in Table 4:

TABLE 4

| | Catalysts | mmol/ OH | wt % | SFT 2 mm | HSA 5 h 3 × 2 mm | HSA 1 d 3 × 2 mm | HSA 7 d 6 mm <> |
|---|---|---|---|---|---|---|---|
| Reference catalysts | DLDBE | 0.7 | 0.9% | 5 min | 25 | 29 | 31 29 |
| | Ti(OnBu)$_4$ | 2.1 | 1.4% | 20 min | NC | NC | NC |
| | Al(OsBu)$_3$ | 2.1 | 1.0% | 25 min | NC | NC | NC |
| | Zr(OnPr)$_4$ | 2.1 | 1.4% | 20 min | NC | NC | NC |
| Ex. 15 Comparative | AlZr(OsBu)$_3$(OnBu)$_4$ | 2.1 | 2.6% | n.d. | 8 | 9 | 13 28 |
| | Al(OsBu)$_3$ | 2.1 | 1.0% | 10 min | C | S | S |
| | Zr(OnBu)$_4$ | 2.1 | 1.6% | | | | |
| Ex. 16 | Al$_2$Zr(OC$_4$H$_9$)$_{10}$ | 2.1 | 3.3% | 25 min | n.d. | 26 | 32 28 |
| Ex. 17 Comparative | AlTi(OsBu)$_3$(OnBu)$_4$ | 2.1 | 2.4% | n.d. | C | 9 | C 19 |
| | Al(OsBu)$_3$ | 2.1 | 1.4% | 6 min | C | 3 | 6 21 |
| | Ti(OnBu)$_4$ | 2.1 | 1.0% | | | | |
| Ex. 18 | Al$_2$Ti(OEH)$_{10}$ | 2.1 | 5.9% | n.d. | n.d. | 22 | 36 31 |
| Comparative | Al(OEH)$_3$ | 4.2 | 3.5% | 20 min | C | C | C |
| | Ti(OEH)$_4$ | 2.1 | 2.4% | | | | |
| Ex. 19 | Al$_2$Ti(OC$_4$H$_9$)$_{10}$ | 2.1 | 3.2% | 20 min | n.d. | 19 | 31 31 |

The results of the tests on the mixed chelate catalysts in the presence of an adhesion promoter are presented in Table 5:

TABLE 5

| | Catalysts | mmol/ OH | wt % | SFT 2 mm | HSA 5 h 3 × 2 mm | HSA 1 d 3 × 2 mm | HSA 7 d 6 mm <> |
|---|---|---|---|---|---|---|---|
| reference catalysts | DLDBE | 0.7 | 0.9% | 5 min | 25 | 29 | 31 29 |
| | Ti(OiPr)$_2$(EAA)$_2$ | 1.8 | 1.5% | 20 min | S | 15c | 28 25 |
| | Al(EAA)$_3$ | 2.1 | 1.0% | 10 min | C | S | C |

TABLE 5-continued

| Catalysts | | mmol/ OH | wt % | SFT 2 mm | HSA 5 h 3 × 2 mm | HSA 1 d | HSA 7 d 6 mm <> |
|---|---|---|---|---|---|---|---|
| Ex. 20 | AlZr(EAA)$_3$(OnPr)$_4$ | 1.3 | 2.0% | 5 min | C | S | 11 23 |
| Comparative | Al(EAA)$_3$ | 1.3 | 1.1% | 17 min | C | C | C |
|  | Zr(OnPr)$_4$ | 1.3 | 0.9% |  |  |  |  |
| Ex. 21 | Al$_2$Zr(EAA)$_6$(OnPr)$_4$ | 1.3 | 3.0% | 12 min | n.d. | 17 | 30 30 |
| Ex. 22 | AlTi(EAA)$_3$(OnBu)$_4$ | 1.5 | 2.0% | 5 min | C | 2 | 16 23 |
| Comparative | Al(EAA)$_3$ | 1.5 | 1.1% | 18 min | C | S | S |
|  | Ti(OnBu)$_4$ | 1.5 | 0.9% |  |  |  |  |

In the presence of the adhesion promoter, it is possible to carry out polycondensation with the tin catalyst (DLDBE). In contrast, the presence of the aminated silane completely inhibits the reactivity of the tin-free catalysts of the prior art.

The heterometallic complexes according to the invention, which do not contain tin, have catalytic activity even in the presence of the adhesion promoter. It was found that the catalyzed reaction was quicker when the molar ratio Al/Zr or Al/Ti was 2.

Example 7: Adhesion Tests

For performing qualitative adhesion tests, a product cord prepared from the formulation described in example 4 and the test catalyst was deposited on plates of glass, concrete (rough side) and anodized aluminum, cleaned and brushed beforehand. After a crosslinking time of 7 days (at 23° C. and 50% RH), manual peeling was performed after making a separation start at the substrate/joint interface. The results are expressed as a function of the type of rupture of the product cord:

AF: adhesive failure (cord detaches from the substrate);
AF+: failure with adhesive tendency, but requiring application of force to detach the cord;
AF++: failure with adhesive tendency, but requiring application of a strong force to detach the cord;
CF: cohesive failure (the cord breaks on application of a very high force, without being detached from the substrate, even partially); in this case there is optimal adhesion to the substrate.

The results are presented in Table 6:

TABLE 6

|  |  | Adhesion to a substrate of: | | |
|---|---|---|---|---|
| | Catalysts | glass | concrete | aluminum |
| Reference catalysts | DLDBE | AF | AF | AF |
|  | Zr(OnPr)$_4$ | CF | AF | CF |
|  | Ti(OnBu)$_4$ | AF | AF+ | AF+ |
|  | Ti(EAA)$_2$(OiPr)$_2$ | AF | CF | CF |
| Ex. 23 | AlZr(OsBu)$_3$ (OnBu)$_4$ | CF | AF | CF |
| Ex. 24 | AlTi(OsBu)$_3$ (OnBu)$_4$ | CF | AF | CF |
| Comparative | Al(OsBu)$_3$ + Ti(OnBu)$_4$ | CF | AF | AF+ |
| Ex. 25 | AlZr(EAA)$_3$(OnPr)$_4$ | CF | CF | CF |
| Ex. 26 | AlTi(EAA)$_3$(OnBu)$_4$ | CF | CF | CF |
| Comparative | Al(EAA)$_3$ + Ti(OnBu)$_4$ | AF+ | CF | AF++ |

Zirconium alkoxide makes it possible to obtain cohesive failure on glass and aluminum, and adhesive failure on concrete. Only the titanium chelate reference catalyst provides adhesion to all three substrates. Regardless of the content of alkoxide catalysts, the catalysts based on aluminum and zirconium allow cohesive failure on glass and aluminum, and adhesive failure on concrete. The catalysts comprising chelate groups make it possible to obtain cohesive failure on all three substrates. Adhesion is lost when mixing of monometallic catalysts is carried out at the time of formulation. The presence of the chelate group supplies adhesion of the elastomer to the substrates. Therefore it is not necessary to add an adhesion promoter as with the tin-based reference. Catalyst preforming is once again indispensable for an optimal result.

Example 8: Colorimetric Tests

In order to carry out qualitative colorimetry tests, a product film with thickness of 2 mm was prepared from the preceding formulation and the test catalyst. After a crosslinking time of 7 days (at 23° C. and 50% RH), the opacity and the yellow color of the film through a white sheet were evaluated qualitatively. The qualitative results are given as a function of the reference catalysts:

− − corresponds to transparent, colorless elastomers,
− corresponds to film with opaque tendency,
+ corresponds to a slightly yellow film,
++ corresponds to a yellow film.

NH denotes that the elastomer is not homogeneous, with appearance of pieces of catalysts that are insoluble in the oil.

The results are presented in Table 7:

TABLE 7

|  |  | colorimetry | |
|---|---|---|---|
| | Catalysts | Opacity | Yellow |
| Reference catalysts | DLDBE | −− | −− |
|  | Zr(OnPr)$_4$ | − | −− |
|  | Ti(OnBu)$_4$ | − | + |
|  | Ti(EAA)$_2$(OiPr)$_2$ | −− | ++ |
| Ex. 27 | AlZr(OsBu)$_3$(OnBu)$_4$ | −− | −− |
| Comparative | Al(OsBu)$_3$ + Zr(OnBu)$_4$ | −− | −− |
| Ex. 28 | AlTi(OsBu)$_3$(OnBu)$_4$ | −− | + |
| Comparative | Al(OsBu)$_3$ + Ti(OnBu)$_4$ | −− | + |
| Ex. 29 | AlZr(EAA)$_3$(OnPr)$_4$ | −− | −− |
| Comparative | Al(EAA)$_3$ + Zr(OnBu)$_4$ | NH | NH and − |
| Ex. 30 | AlTi(EAA)$_3$(OnBu)$_4$ | − | ++ |
| Comparative | Al(EAA)$_3$ + Ti(OnBu)$_4$ | NH | NH and + |

The films containing titanium-based catalysts are slightly, or even completely yellow. Those catalyzed by mixtures of monometallic species are not homogeneous. In contrast, the elastomers based on aluminum and zirconium are perfectly translucent.

The invention claimed is:
1. A composition that can be cured in the presence of water or atmospheric moisture comprising:

(A) at least one polyorganosiloxane A having one or more condensable or hydrolyzable and condensable group(s), and
(B) at least one compound C, capable of catalyzing the condensation reaction of the condensable or hydrolyzable and condensable groups of the polyorganosiloxane A, and which is a heterometallic complex whose chemical formula comprises:
at least two different metal atoms M and M', M being an atom selected from the group consisting of the atoms in columns 2 and 13 of the periodic table and M' being an atom selected from the group consisting of the atoms in column 4 of the periodic table, and
at least one alkoxide ligand or chelating ligand,
in which the at least one polyorganosiloxane A comprises:
(i) at least two siloxyl units of the following formula (V):

$$R^4_a Z_b \, SiO_{\frac{4-(a+b)}{2}} \quad (V)$$

in which:
the symbols $R^4$, which may be identical or different, represent monovalent $C_1$ to $C_{30}$ hydrocarbon radicals,
the symbols Z, which may be identical or different, each represent a hydrolyzable and condensable group or a hydroxyl group,
a is equal to 0, 1 or 2, b is equal to 1, 2 or 3, the sum a+b is equal to 1, 2 or 3, and
(ii) optionally one or more siloxyl unit(s) of the following formula (VI):

$$R^5_c \, SiO_{\frac{4-c}{2}} \quad (VI)$$

in which:
the symbols $R^5$, which may be identical or different, represent monovalent $C_1$-$C_{30}$ hydrocarbon radicals optionally substituted with one or more halogen atoms or with amino, ether, ester, epoxy, mercapto or cyano groups, and
the symbol c is equal to 0, 1, 2 or 3.

2. The composition as claimed in claim 1, wherein compound C is a heterometallic complex whose chemical formula comprises:
at least two different metal atoms M and M', M being an atom of magnesium (Mg) or of aluminum (Al), and M' being an atom of titanium (Ti) or of zirconium (Zr), and
at least one alkoxide ligand or chelating ligand.

3. The composition as claimed in claim 2, wherein compound C is selected from the group consisting of:
a heterometallic complex whose chemical formula comprises:
at least two different metal atoms M and M', M being aluminum and M' being zirconium and in which the molar ratio Al/Zr=0.5, 1 or 2; and
at least one alkoxide ligand or chelating ligand; and
a heterometallic complex whose chemical formula comprises:
at least two different metal atoms M and M', M being aluminum and M' being titanium and in which the molar ratio Al/Ti=1 or 2, and
at least one alkoxide ligand or chelating ligand.

4. The composition as claimed in claim 1 wherein compound C is a heterometallic alkoxide complex whose chemical formula comprises:
at least two different metal atoms M and M', M being magnesium or aluminum and M' being titanium or zirconium, and
at least one alkoxide ligand.

5. The composition as claimed in claim 4, wherein said heterometallic alkoxide complex is selected from the group consisting of:
a heterometallic alkoxide complex whose chemical formula comprises at least two different metal atoms M and M', M being aluminum and M' being zirconium, at least one alkoxide ligand of chemical formula O-(linear or branched $C_3$-$C_{12}$ alkyl), and in which the molar ratio Al/Zr has the value 0.5, 1 or 2;
a heterometallic alkoxide complex whose chemical formula comprises at least two different metal atoms M and M', M being magnesium and M' being zirconium, at least one alkoxide ligand of chemical formula O-(linear or branched $C_2$-$C_{12}$ alkyl), and in which the molar ratio Mg/Zr has the value 0.5, 1, 2, 3 or 4; and
a heterometallic alkoxide complex whose chemical formula comprises at least two different metal atoms M and M', M being aluminum and M' being titanium, at least one alkoxide ligand of chemical formula O-(linear or branched $C_3$-$C_{12}$ alkyl), and in which the molar ratio Al/Ti has a value of 1 or 2.

6. The composition as claimed in claim 1 wherein compound C is a heterometallic chelated complex whose chemical formula comprises:
at least two different metal atoms M and M', M being magnesium or aluminum and M' being titanium or zirconium, and
at least one chelate ligand.

7. The composition as claimed in claim 1 further comprising a crosslinking agent B.

8. The composition as claimed in claim 7, in which the crosslinking agent B is a silicon compound having the following formula (XIII):

$$R^{20}_{(4-j)} SiY_j \quad (XIII)$$

in which:
the symbol $R^{20}$ is a monovalent hydrocarbon radical comprising from 1 to 30 carbon atoms,
the symbols Y, which may be identical or different, are selected from the group consisting of the alkoxy, alkoxy-alkylene-oxy, amino, amido, acylamino, aminoxy, iminoxy, ketiminoxy, acyloxy or enoxy groups,
the symbol j=2, 3 or 4.

9. The composition as claimed in claim 1, additionally comprising an adhesion promoter E.

10. A single-component composition RTV-1 that is in a single airtight package P and comprises:
a) at least one polyorganosiloxane A,
b) at least one crosslinking agent B,
c) a catalytically effective amount of at least one compound C, and
d) optionally at least one filler D,
wherein A and C are as defined in claim 1.

11. A silicone elastomer obtained by bringing the contents of package P of the single component composition RTV-1 as claimed in claim 10 into contact with atmospheric moisture and leaving said contents to cure.

12. A two-component composition RTV-2, precursor of the composition as claimed in claim 1 which is in two separate packages P1 and P2 wherein:
a) package P1 is airtight and comprises:
a catalytically effective amount of at least one compound C, and
at least one crosslinking agent B, and
b) package P2 contains neither said compound C nor said crosslinking agent B and comprises:
per 100 parts by weight of at least one polyorganosiloxane A, and
from 0 to 10 part(s) by weight of water,
wherein A and C are as defined in claim 1.

13. A silicone elastomer obtained by mixing the contents of packages P1 and P2 of the two-component composition RTV-2 as claimed in claim 12 and leaving the mixture to cure.

14. A silicone elastomer obtained:
after leaving the composition as defined in claim 1 to cure in the presence of water or atmospheric moisture.

15. A process for coating a composition according to claim 1 on a flexible substrate S comprising a), b) and c):
a) preparing the composition
b) then depositing said composition continuously or discontinuously on said flexible substrate S, and
leaving said silicone composition to cure in the presence of moisture supplied by the ambient air or by adding water beforehand so as to form a silicone elastomer.

16. The composition as claimed in claim 1, wherein said compound C is a heterometallic alkoxide complex selected from the group consisting of $AlZr(O\text{-butyl})_4(O\text{-sec-butyl})_3$, $Al_2Zr(O\text{ n-butyl})_4(O\text{ sec-butyl})_6$, $AlZr_2(O\text{-n-Butyl})_{11}$, $AlTi(O\text{-sec-butyl})_3(O\text{-n-butyl})_4$ and $Al_2Ti(O\text{-n-butyl})_{10}$.

17. The composition as claimed in claim 1 wherein compound C is a heterometallic chelated complex selected from the group consisting of:
a heterometallic chelated complex whose chemical formula comprises:
at least two different metal atoms M and M', M being aluminum and M' being zirconium,
at least one chelating ligand selected from the group consisting of ethyl acetoacetate, propyl acetoacetate and diisopropyl malonate,
optionally at least one alkoxide ligand of chemical formula O-(linear or branched $C_3$ or $C_4$ alkyl), and
having a molar ratio Al/Zr=1 or 2;
a heterometallic chelated complex whose chemical formula comprises:
at least two different metal atoms M and M', M being aluminum and M' being zirconium,
at least one chelating ligand selected from the group consisting of ethyl acetoacetate, propyl acetoacetate and diisopropyl malonate,
having a molar ratio Al/Zr=1 or 2, and not comprising an alkoxide ligand;
a heterometallic chelated complex whose chemical formula comprises:
at least two different metal atoms M and M', M being magnesium and M' being zirconium,
at least one ethyl acetoacetate chelating ligand, and
having a molar ratio Mg/Zr=1;
a heterometallic chelated complex whose chemical formula comprises:
at least two different metal atoms M and M', M being aluminum and M' being titanium,
at least one chelating ligand selected from the group consisting of ethyl acetoacetate and propyl acetoacetate,
optionally at least one alkoxide ligand of chemical formula O-(linear or branched $C_3$ or $C_4$ alkyl), and
having a molar ratio Al/Ti=1; and
a heterometallic chelated complexes whose chemical formula comprises:
at least two different metal atoms M and M', M being magnesium and M' being titanium,
at least one ethyl acetoacetate chelating ligand,
optionally at least one alkoxide ligand of chemical formula O-(linear or branched $C_3$ alkyl), and
having a molar ratio Mg/Ti=1.

18. The composition as claimed in claim 1, wherein compound C is a heterometallic chelated complex selected from the group consisting of $AlZr(\text{ethyl acetoacetate})_3(O\text{-n-propyl})_4$, $Al_2Zr(\text{ethyl acetacetate})_6(O\text{-n-propyl})_4$, $AlZr(\text{ethyl acetoacetate})_7$, $Al_2Zr(\text{ethyl acetoacetate})_{10}$ and $AlTi(\text{ethyl acetoacetate})_3(O\text{-n-butyl})_4$.

19. A method comprising catalyzing a condensation reaction of the condensable or hydrolyzable and condensable groups of a polyorganosiloxane A) having one or more condensable or hydrolyzable and condensable group(s) with a heterometallic complex whose chemical formula comprises at least two different metal atoms M and M', M being an atom selected from the group consisting of the atoms in columns 2 and 13 of the periodic table and M' being an atom selected from the group consisting of the atoms in column 4 of the periodic table, and at least one alkoxide ligand or chelating ligand.

\* \* \* \* \*